(12) United States Patent
Simonson

(10) Patent No.: US 7,083,622 B2
(45) Date of Patent: Aug. 1, 2006

(54) ARTIFICIAL FACET JOINT AND METHOD

(76) Inventor: Peter M. Simonson, 85 Palm Ave., Miami Beach, FL (US) 39139

( * ) Notice: Subject to any disclaimer, the term of this patent is extended or adjusted under 35 U.S.C. 154(b) by 236 days.

(21) Appl. No.: 10/780,426

(22) Filed: Feb. 17, 2004

(65) Prior Publication Data

US 2005/0101956 A1     May 12, 2005

Related U.S. Application Data

(63) Continuation-in-part of application No. 10/720,659, filed on Nov. 24, 2003, which is a continuation-in-part of application No. 10/704,868, filed on Nov. 10, 2003.

(51) Int. Cl.
*A61B 17/56* (2006.01)
(52) U.S. Cl. .............................. 606/61; 606/60; 606/53
(58) Field of Classification Search ................... 606/61
See application file for complete search history.

(56) References Cited

U.S. PATENT DOCUMENTS

| | | |
|---|---|---|
| 3,219,575 A | 11/1965 | Chapman et al. |
| 3,242,922 A | 3/1966 | Thomas |
| 3,565,066 A | 2/1971 | Roaf |
| 4,269,178 A | 5/1981 | Keene |
| 4,272,401 A | 6/1981 | Mohan et al. |
| 4,361,141 A | 11/1982 | Tanner |
| 4,369,769 A | 1/1983 | Edwards |
| 4,369,770 A | 1/1983 | Bacal et al. |
| 4,382,438 A | 5/1983 | Jacobs |
| 4,386,603 A | 6/1983 | Mayfield |
| 4,404,967 A | 9/1983 | Bacal et al. |
| 4,409,968 A | 10/1983 | Drummond |
| 4,411,259 A | 10/1983 | Drummond |
| 4,419,026 A | 12/1983 | Leto |
| 4,422,451 A | 12/1983 | Kalamchi |
| 4,448,191 A | 5/1984 | Rodnyansky et al. |
| 4,567,884 A | 2/1986 | Edwards |
| 4,611,582 A | 9/1986 | Duff |
| 4,662,365 A | 5/1987 | Gotzen et al. |
| 4,743,260 A | 5/1988 | Burton |
| 4,773,402 A | 9/1988 | Asher et al. |
| 4,815,453 A | 3/1989 | Cotrel |
| 4,836,196 A | 6/1989 | Park et al. |
| 4,854,304 A | 8/1989 | Zielke |
| 4,887,595 A | 12/1989 | Heinig et al. |

(Continued)

FOREIGN PATENT DOCUMENTS

WO    WO03/101350 A1    12/2003

OTHER PUBLICATIONS

Spine-health.com, "Facet Technologies," http://www.spine-health.com/research/discupdate/artificial/artificial06.html.

(Continued)

*Primary Examiner*—Brian E. Pellegrino
*Assistant Examiner*—Robert W. Amareld, Jr.
(74) *Attorney, Agent, or Firm*—Akerman Senterfitt; Micahel K. Dixon

(57) ABSTRACT

An artificial facet joint includes a spinal implant rod and a connector. The connector includes a screw and a rod connecting member having structure for engagement of the rod. The rod connecting member is pivotally engaged to the screw. The rod may also be held slideably within the connector enabling the rod to be moved relative to the connector.

16 Claims, 19 Drawing Sheets

U.S. PATENT DOCUMENTS

| | | | | |
|---|---|---|---|---|
| 4,887,596 A | | 12/1989 | Sherman | |
| 4,946,458 A | | 8/1990 | Harms et al. | |
| 4,950,269 A | | 8/1990 | Gaines, Jr. | |
| 4,987,892 A | | 1/1991 | Krag et al. | |
| 5,002,542 A | | 3/1991 | Frigg | |
| 5,005,562 A | | 4/1991 | Cotrel | |
| 5,024,213 A | | 6/1991 | Asher et al. | |
| 5,102,412 A | | 4/1992 | Rogozinski | |
| 5,127,912 A | | 7/1992 | Ray et al. | |
| 5,129,900 A | | 7/1992 | Asher et al. | |
| 5,133,717 A | | 7/1992 | Chopin | |
| 5,147,360 A | | 9/1992 | Dubousset | |
| 5,181,917 A | | 1/1993 | Rogozinski | |
| 5,209,752 A | | 5/1993 | Ashman et al. | |
| 5,246,442 A | | 9/1993 | Ashman et al. | |
| 5,257,993 A | | 11/1993 | Asher et al. | |
| 5,261,909 A | | 11/1993 | Sutterlin et al. | |
| 5,282,801 A | | 2/1994 | Sherman | |
| 5,282,901 A | | 2/1994 | Reinhard | |
| 5,312,404 A | | 5/1994 | Asher et al. | |
| 5,415,661 A | | 5/1995 | Holmes | |
| 5,425,732 A | * | 6/1995 | Ulrich | 606/61 |
| 5,437,669 A | * | 8/1995 | Yuan et al. | 606/61 |
| 5,437,670 A | | 8/1995 | Sherman et al. | |
| 5,437,671 A | * | 8/1995 | Lozier et al. | 606/61 |
| 5,474,551 A | | 12/1995 | Finn et al. | |
| 5,498,262 A | | 3/1996 | Bryan | |
| 5,549,608 A | | 8/1996 | Errico et al. | |
| 5,554,157 A | | 9/1996 | Errico et al. | |
| 5,562,662 A | | 10/1996 | Brumfield et al. | |
| 5,569,247 A | | 10/1996 | Morrision | |
| 5,571,191 A | | 11/1996 | Fitz | |
| 5,591,166 A | | 1/1997 | Bernhardt et al. | |
| 5,611,800 A | | 3/1997 | Davis et al. | |
| 5,672,175 A | | 9/1997 | Martin | |
| 5,693,053 A | | 12/1997 | Estes | |
| 5,716,357 A | | 2/1998 | Rogozinski | |
| 5,800,435 A | | 9/1998 | Errico et al. | |
| 5,876,459 A | | 3/1999 | Powell | |
| 5,891,145 A | | 4/1999 | Morrision et al. | |
| RE36,758 E | | 6/2000 | Fitz | |
| 6,183,473 B1 | | 2/2001 | Ashman | |
| 6,210,413 B1 | | 4/2001 | Justis et al. | |
| 6,248,105 B1 | | 6/2001 | Schlapfer et al. | |
| 6,328,739 B1 | | 12/2001 | Liu et al. | |
| 6,332,887 B1 | * | 12/2001 | Knox | 606/87 |
| 6,413,257 B1 | | 7/2002 | Lin et al. | |
| 6,443,956 B1 | | 9/2002 | Ray | |
| 6,554,831 B1 | | 4/2003 | Rivard et al. | |
| 6,565,565 B1 | | 5/2003 | Yuan et al. | |
| 6,579,319 B1 | | 6/2003 | Goble et al. | |
| 6,623,485 B1 | | 9/2003 | Doubler et al. | |
| 6,648,887 B1 | | 11/2003 | Ashman | |
| 2003/0004572 A1 | | 1/2003 | Goble et al. | |
| 2003/0028250 A1 | | 2/2003 | Reiley et al. | |
| 2003/0144665 A1 | * | 7/2003 | Munting | 606/61 |
| 2005/0261682 A1 | * | 11/2005 | Ferree | 606/61 |

OTHER PUBLICATIONS

Zimmer Spine, "DYNESYS, The Dynamic Stabilization System (U.S. only)," http://www.zimmerspine.com/spine/products/lumbar/dynesys/index.

* cited by examiner

ARTIFICIAL FACET JOINT AND METHOD

CROSS-REFERENCE TO RELATED APPLICATIONS

This application is a continuation-in-part application of U.S. patent application Ser. No. 10/720,659, filed Nov. 24, 2003, which is a continuation-in-part application of U.S. patent application Ser. No. 10/704,868, filed Nov. 10, 2003.

FIELD OF THE INVENTION

This invention relates generally to the field of artificial joints and more particularly to artificial joints and ligaments.

BACKGROUND OF THE INVENTION

Each vertebra in the human spine has two sets of joints which interact with adjacent upper and lower joints. These joints are known as the facet joints, and are otherwise known as the zygapophyseal or apophyseal joints. Two joints are formed on each lateral side of the vertebra. The superior articular facet faces upward and the inferior articular facet faces downward, such that the superior articular facet of a lower vertebrae abuts the inferior articular facet of an adjacent upper vertebrae. The facet joints are located on the posterior of the spine adjacent the pedicle, lamina, and transverse process. The facet joints generally are hinge-like and allow limited flexion, extension, and twisting motion, while preventing excessive motion which could damage the spinal chord.

Various spinal reconstructive or treatment procedures require the removal of the facet joint and ligament structures. The joint and ligament must then be reconstructed artificially. Known artificial facet joints fail to provide the rigidity that is necessary to support the spine while permitting the flexibility to reassemble the facet joint.

SUMMARY OF THE INVENTION

An artificial facet joint includes a pair of connectors. Each connector comprises a first device connecting member having structure for sliding engagement of a rod and a second device connecting member having structure for sliding engagement of a screw. The first device connecting member and second device connecting member are rotatably engaged to one another. A spinal implant rod and a pair of spinal implant screws are provided. The first device connecting member of each of the connectors is slideably engaged to the rod. The second device connecting member of each of the connectors is slideably engaged to a respective one of the pair of spinal implant screws. The screws can be engaged to the pedicles on one lateral side of adjacent vertebra and the rods and connectors will limit movement of the joint. Structure for securing the spinal implant rod against axial movement relative to the spine can be provided. The structure for sliding engagement of the rod can be an aperture and the structure for sliding engagement of a screw can be an aperture. The apertures of the first device connecting member and the second device connecting member can comprise a reduced friction coating.

The artificial facet joint can further comprise a second pair of connectors, a second spinal implant rod and a second pair of second implant screws. The second pair of screws can be engaged to the pedicles of the other lateral side of the adjacent vertebra and the second rod and second pair of connectors will limit movement of the joint on the other lateral side of the adjacent vertebra. A transverse member can be connected between the first and second rod. The transverse member can be slideably engaged to the first and second rods. The transverse member can alternatively be connected between screws.

The artificial facet joint can further comprise structure for securing the rod to a portion of the spine. This structure can comprise a clamp for the rod and structure for securing the clamp to a screw. Alternatively, the structure can comprise blocking members on the rod.

The spinal implant rod can include structure for engaging the first device connecting member so as to limit the sliding movement of the rod relative to the first device connecting member. The spinal implant screw can comprise structure for engaging the second device connecting member so as to limit the sliding movement of the rod relative to the second device connecting member.

A connector for an artificial facet joint includes a first device connecting member having structure for sliding engagement of a spinal implant rod and a second device connecting member having structure for sliding engagement of a spinal implant screw. The first device connecting member and second device connecting member are rotatably engaged to one another. The structure for engaging the first device connecting member can be an aperture and the structure for engaging the second device connecting member can be an aperture. The apertures of the first device connecting member and the second device connecting member can comprise a reduced friction coating.

A connector assembly for an artificial joint can include a connection device having a first connecting portion with structure for sliding engagement of a rod and a second connecting portion with sliding engagement of a screw. A spinal implant rod is slideably engaged to the first connecting portion and the spinal implant screw is slideably engaged to the second connecting portion. The structure for engaging the rod can be an aperture and the structure for engaging the screw can be an aperture. The spinal implant rod can comprise structure for engaging the first connecting portion so as to limit the sliding movement of the rod relative to the first connecting portion. The spinal implant screw can comprise structure for engaging the second connecting portion so as to limit the sliding movement of the rod relative to the second connecting portion.

An artificial facet joint includes a spinal implant rod and connector. The connector comprises a first device connecting member having structure for sliding engagement of said rod and a second device connecting member having structure for sliding engagement of a screw. The first device connecting member and second device connecting member are rotatably engaged to one another. Structure is provided for securing the spinal implant rod against axial movement relative to the spine.

A method for creating an artificial facet joint includes the step of providing a first pair of connectors. Each connector comprises a rod connecting member having an aperture for engaging a rod, a screw connecting member having an aperture for engaging a screw, the rod connecting member and the screw connecting member being rotatably engaged to one another. A first screw is secured to a pedicle of a first vertebra. A second screw is secured to a pedicle of a second vertebra. The screws can be positioned in the plane of the facet. The screw connecting member of the first connector is slideably engaged to the first screw, and the screw connecting member of the second connector is slideably engaged to the second screw. A spinal implant rod is slideably engaged to the rod connecting member of the first connector and to the rod connecting member of the second connector. The rod is then secured.

A second pair of connectors can be provided. Each connector comprises a rod connecting member having an aperture for engaging a rod and a screw connecting member having an aperture for engaging a screw. The rod connecting member and the screw connecting member are rotatably engaged to one another. A first screw is secured to a pedicle on an opposite lateral side of a first vertebra. A second screw is secured to a pedicle on an opposite side of a second vertebra. The screw connecting member of the first connector is slideably engaged to the first screw and the screw connecting member of the second connector is slideably engaged to the second screw. A spinal implant rod is slideably engaged to the rod connecting member of the first connector of the second pair of connectors and to the rod connecting member of the second connector on the opposite lateral side of the vertebra. The second rod is secured between the second pair of connectors. A transverse member can be attached between the spinal implant rods.

A spinal joint assembly includes a spinal joint device joined to a spinal implant rod which is capable of post-operative sliding movement relative to the rod. Structure can be provided for limiting the length of sliding movement between the spinal implant rod and the spinal joint device. A method of connecting a spinal joint assembly to a spine includes the steps of connecting a spinal implant rod to a spine and attaching a spinal joint device to the rod. The device is capable of post-operative sliding movement relative to the rod.

A spinal joint assembly comprises a spinal joint device joined to a spinal implant screw. The spinal joint device is capable of post-operative sliding movement relative to the screw. Structure can be provided for limiting the length of sliding movement between the spinal implant screw and the spinal joint device. A method of connecting a spinal joint assembly to a spine includes the steps of connecting a spinal implant screw having a long axis to the spine. A spinal implant device is connected to the screw and is capable of post-operative sliding movement along the long axis of the screw.

A bone implant screw is provided for securing connected implants to a spine. The bone implant screw upon installation in the spine permits dorsal movement relative to itself and the connected implants. The screw can comprise a post. The movement permitted by the screw can further comprise rotation of the connected implants about an axis of the screw. The screw can comprise structure for limiting dorsal movement of the connected implants beyond a range of movement.

An artificial facet joint comprises a spinal implant rod and a connector. The connector comprises a screw and a rod connecting member having structure for engagement of the rod. The rod connecting member is pivotally engaged to the screw.

The rod connecting member can be detachable from the screw. The pivoting can be about a pivot point substantially in the long axis of the screw. The connector can be polyaxially pivotable relative to the rod.

The connector can engage the rod to prevent sliding movement of the rod relative to the connector. The connector can alternatively permit sliding movement of the rod relative to the connector. The connector can comprise a saddle portion and a detachable cap for enclosing the rod within the saddle portion.

Structure can be provided for limiting the angulation of the rod connector relative to the screw. This structure can provide increasing resistance as the degree of angulation increases. The structure can comprise a stop on at least one of the connector and the screw. The stop can comprise an elastic material.

The artificial facet joint can further comprise a second spinal implant rod and a second connector. The second connector can comprise a screw and a rod connecting member having structure for engagement of the rod. The rod connecting member is pivotally engaged to the screw. A transverse crosslinking member engages and connects the spinal rods. The crosslinking member can engage the rods and contact the connectors to limit movement of the spinal rods relative to the connectors.

An artificial facet joint can comprise a spinal implant rod and a connector with a rod connecting portion and a screw portion. The connector permits sliding movement of the rod relative to the rod connecting portion and pivoting of the rod relative to the screw portion. The pivot can be about a pivot point substantially in the long axis of the screw.

An artificial facet joint can comprise a spinal implant rod and a connector with a rod connecting portion and a screw portion. The connector engages the rod to prevent sliding movement of the rod relative to the rod connecting portion and permits pivoting of the rod relative to the screw portion. The pivot can be about a pivot point substantially in the long axis of the screw.

An artificial facet joint can comprise a spinal implant rod and a fixation connector with a rod engaging portion and a screw portion. The fixation connector engages the rod to prevent sliding movement of the rod relative to the rod engaging portion and permits pivoting of the rod relative to the screw portion. A sliding connector has a rod connecting portion and a screw portion. The sliding connector permits sliding movement of the rod relative to the rod connecting portion and pivoting of the rod relative to the screw portion.

An artificial facet joint comprises a spinal rod that is substantially parallel to the spinal column and can span at least three vertebrae.

An artificial facet joint comprises a spinal rod that articulates in the sagittal plane.

An artificial facet joint can connect vertebral bodies of adjacent vertebrae on the same lateral side of the spine with a single rod.

The artificial facet joints can be implanted by suitable methods. In one method, only percutaneous incisions are needed to install the artificial facet joint.

An artificial facet joint can comprise a spinal implant rod and at least one connector for sliding engagement of the rod. The connector can further have structure for engaging the spine. The rod has-d shape defining a desired bending of the spine, such that bending of the spine will cause sliding movement of the connector relative to the rod. The rod will guide the connector according to a path defined by the rod.

An artificial facet joint can comprise a spinal implant rod and at least one connector for engaging the rod to a screw. The connector is movable over the screw. The screw is shaped to provide a path for guiding the motion of the spine during bending of the spine.

Each of these connectors may be used to strengthen a facet joint in a spine without fusing adjacent vertebrae together and causing a patient to be less flexible. A facet joint may be stabilized by securing a first rod to a spine substantially parallel to the spine in a manner that substantially prevents movement of the first rod relative to the spine and parallel to a longitudinal axis of the first rod. The first post may, but is not limited to being, attached to the spine using threads, a hook, an adhesive, or other such devices. The first post may have a generally cylindrical cross-section or other cross-sections enabling a connector to slide or move generally perpendicular to the post. The first post may be secured to the spine so that the at least one first post extends generally orthogonal to the spine. The first rod may be attached to the first post in a slideable engagement so that the first rod may move generally parallel to the longitudinal axis of the first rod and may move relative to the first post.

The method of strengthening a facet joint may also include securing a second rod to the first vertebrae of a spine substantially parallel to the spine and substantially parallel to the first rod in a manner that substantially prevents movement of the first rod relative to the spine and movement parallel to a longitudinal axis of the second rod. The second post may be secured to the vertebrae to which the first rod is secured, and the second rod may be attached to the at least one second post in a slideable engagement so that the second rod may move generally parallel to the longitudinal axis of the second rod and move relative to the at least one second post. A cross-support member may be coupled to the first and second rods to stabilize the first and second rods. The cross-support member may have an adjustable length.

The first and second rods may be attached to the spine either at a vertebrae or a sacrum. The rods may be attached to the spine using a post or other attachment device. The rods may be attached with mechanical connectors that may enable the first and second rods to move vertically along the posts or may prevent such movement by fixedly attaching the mechanical connectors to the posts. Threaded devices may be used to limit such movement. The mechanical connectors may rotate about an axis generally parallel to the longitudinal axis of the first rod. The mechanical connector may also rotate generally perpendicular to the longitudinal axis of the first rod. The rods may have a single longitudinal axis or may include two or more longitudinal axes to control movement of the vertebrae along the spine. In other words, the rods may be nonlinear to control movement of the vertebrae.

The invention also includes a method of stabilizing a spine by securing a first rod to a spine substantially parallel to the spine in a manner that substantially prevents movement of the first rod relative to the spine, securing a second rod to a vertebrae of a spine substantially parallel to the spine in a manner that substantially prevents movement of the second rod relative to the vertebrae, and coupling the first and second rods together along the rods at a point between a location where the first rod is secured to the spine and a location where the second rod is secured to the vertebrae in a manner enabling the rods to move generally parallel to each other. This configuration enables the rods to move relative to each other generally along each other's longitudinal axis. The first and second rods may be secured to the spine and vertebrae with posts. In at least one embodiment, the first and second rods may be coupled together using a slider so that the rods may move generally along each other's longitudinal axis. The slider may be fixedly or slideably coupled to the first rod and slideable coupled to the second rod.

These and other embodiments are described in detail below.

BRIEF DESCRIPTION OF THE DRAWINGS

There are shown in the drawings embodiments which are presently preferred, it being understood, however, that the invention is not limited to the precise arrangements and instrumentalities shown, wherein.

DETAILED DESCRIPTION OF THE INVENTION

Figure 1:
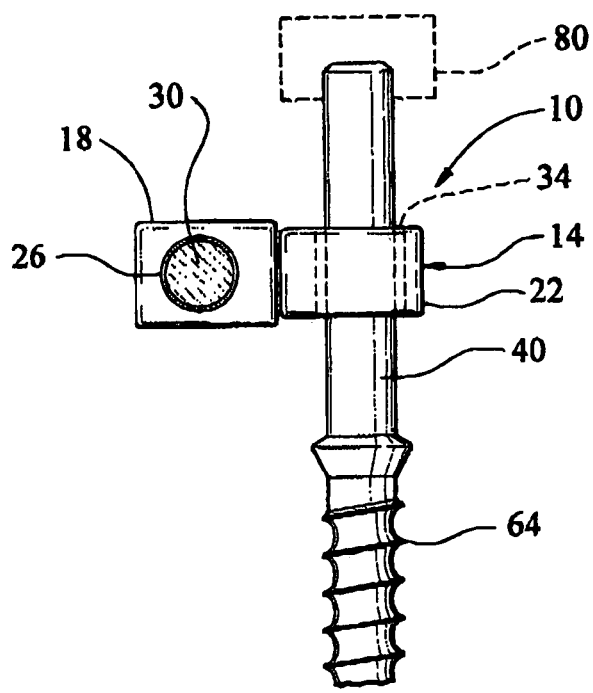
FIG. 1 is a side elevation of a connector.
Figure 2:
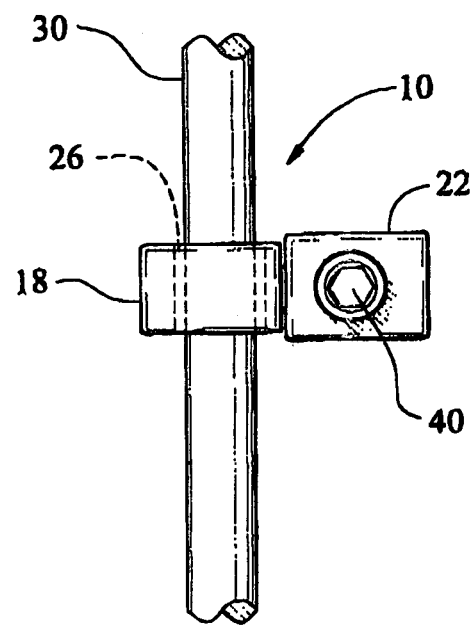
FIG. 2 is a plan view.

There is shown in FIGS. 1–44 a connector assembly for an artificial facet joint according to the invention. The connector assembly 10 includes a connector 14 having a first device connecting member 18 and a second device connecting member 22. The first device connecting member 18 has structure for sliding engagement of a spinal implant rod 30. The second device connecting member 22 has structure for sliding engagement of a spinal implant screw 40. The structure for slideably engaging the spinal implant rod 30 can be an aperture 26 for receiving the rod 30. The structure for slideably engaging the spinal implant screw 40 can be an aperture 34 for receiving the screw 40. Other structure is possible. The apertures 26 and 34 can be larger in diameter than the cross-sectional diameter of the rod 38 and screw 40, if desired, to permit movement of the first device connecting member 18 relative to the rod 30 as shown by arrow 46 in FIG. 3, as well as transverse movement to the extent of the size of the aperture 26. Similarly, the size of the aperture 34 can permit movement of the second device connecting member 22 relative to the screw 40, as shown by arrow 50 in FIG. 3, as well as transverse movement to the extent of the size of the aperture 34. Also, the first device connecting member 18 can rotate about the rod 30, as shown by arrow 54, and second device connecting member can rotate about the screw 40, as shown by arrow 58.

Figure 3:
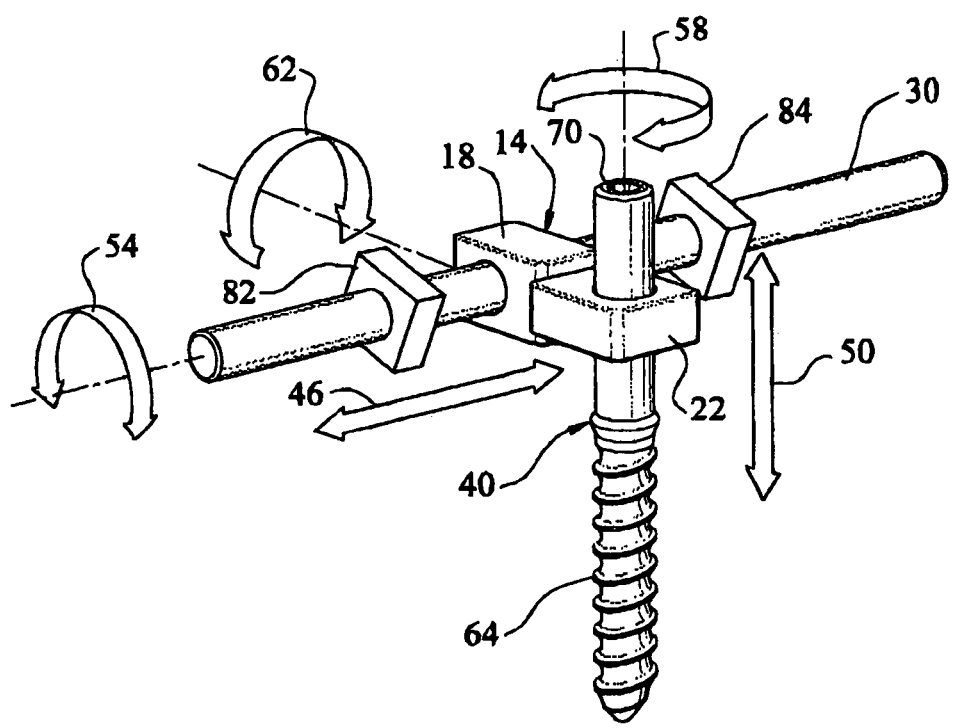
FIG. 3 is a perspective view of a connection assembly with a connector, spinal implant rod, and a spinal implant screw, illustrating by arrows the motion that is possible.

The first device connecting member 18 and second device connecting member 22 are rotationally engaged to one another such that the first device connecting member 18 can rotate relative to the second device connecting member 22 as indicated by arrow 62 in FIG. 3. Any suitable connecting structure which will secure the first connecting member 18 to the second connecting member 22 and permit this rotation can be used.

The screw 40 can be any suitable spinal implant or pedicle screw or bolt. Threads 64 are provided for engaging the bone, however, other constructions for securing the device to bone are possible. The elongated shaft 70 can be of sufficient length that the second device connecting member 22 does not become disengaged. The shape of the screw head shaft may be varied to produce a desired motion path similar to a particular facet joint. For example, the screw shaft may have a curved shape. Alternatively, it is possible to place a head or cap unit on the screw 40. The head unit 80 (phantom lines in FIG. 1) would be an enlarged portion which could either be detachable from the screw 40 or form a permanent part thereof. The head 80 has a diameter larger than that of the aperture 34 such that the second device connecting member 22 cannot be removed from the screw 40. Other structure is possible.

The screw can also have an irregular cross section, such as an elipse, so that a connecting device can be attached which makes for the irregular shape and prevents rotation of the connecting device relative to the screw. The screw can alternatively have a protrusion or other engagement structure which engages a corresponding recession or cooperating engagement structure in the connecting device to prevent rotation.

It is also possible to limit the range of movement of the rod 30 within the first device connecting member 18. This can be accomplished by a blocking portion 82 that is provided on the rod 30 and is large enough so as not to permit passage through the aperture 26 of the first device connecting member 18. A second blocking member 84 can be provided on a portion of the rod 30 on the other side of the first device connecting member 22. The blocking members 82 and 84 can be fixed to the rod 30, or can be slideably engaged to the rod 30 and secured by suitable structure such as a set screw. Each of these blocking devices could provide progressive resistance (proportional to distance) with or without elastic properties. The blocking members 82 and 84 can be formed from a rigid material, or from an elastic material which will mimic the action of the ligaments. The elastic material can be such that a force is applied by the elastic material which is proportional to the distance traveled. Other structure is possible. Varying these parameters allows for closer reproduction of the ligament functions. The blocking devices can also prevent removal of the rod from the connectors. The blocking devices could also be connected to other parts of the construct, thus preventing any undesirable movement of the screw with respect to the vertebral body. For example, this could ensure a screw does not back out of the vertebral body. Such blocking devices could also be integral into the connector itself with the use of set screws, channels, and the like.

Figure 4:
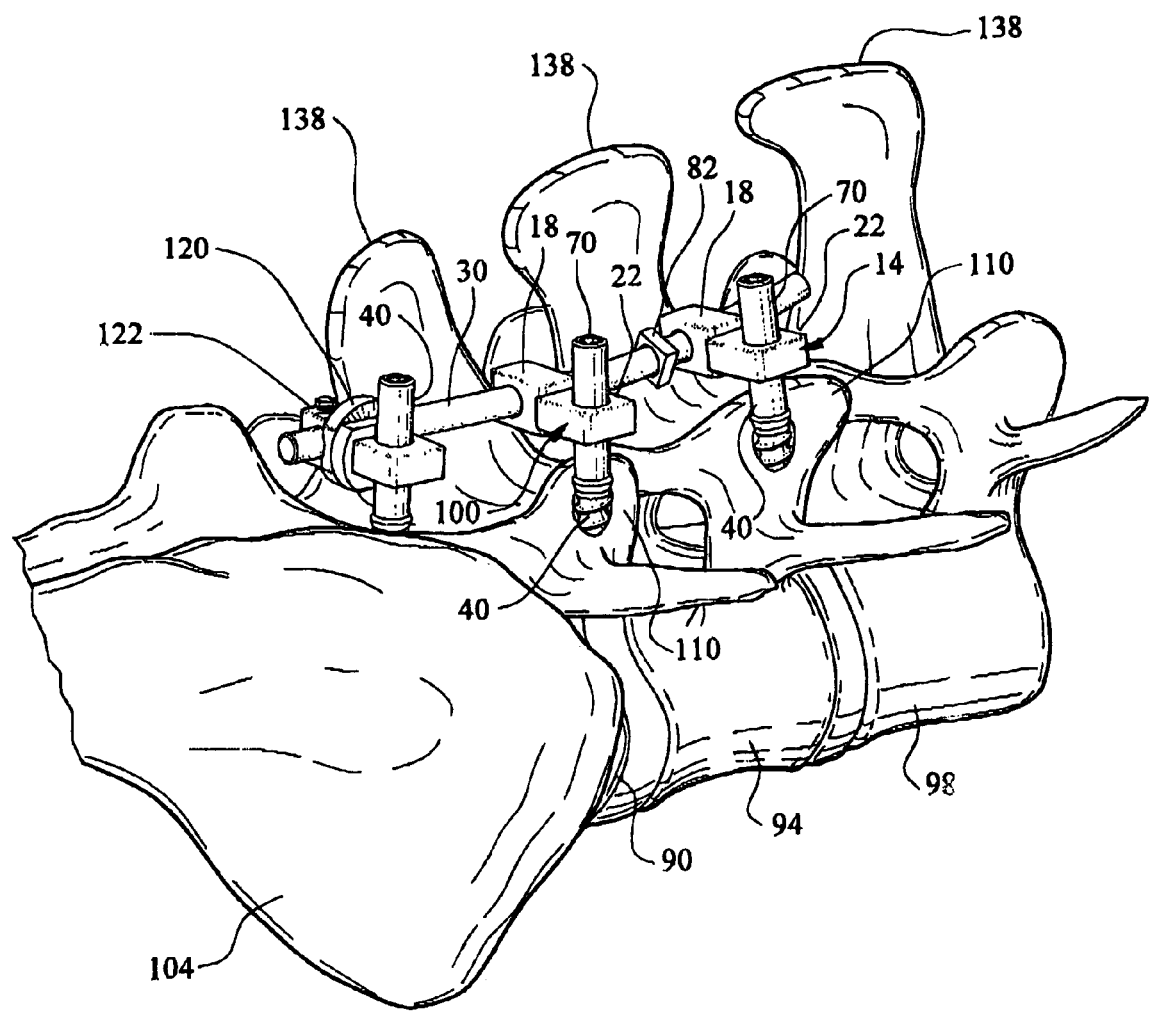
FIG. 4 is a perspective view of an artificial facet joint according to the invention as implanted in a spine.

An installation of an artificial facet joint according to the invention is shown in FIG. 4. The invention can be utilized with any vertebra; however, there is shown the lumbar vertebrae 90, 94, and 98 adjacent to sacrum 104. The rod 30 is slideably engaged to the first connecting member 18 of the connector 14. The second device connecting member 22 is slideably engaged to the elongated shaft 70 of the pedicle screw 40. The apertures 26 and 34 can be coated with a friction reducing coating. The pedicle screw 40 is secured to the pedicle 110 of the vertebra 94. The screw 40 can be secured in the plane of the existing or former facet so as to better mimic the natural facet. If the natural facet is in existence, the artificial facet will provide reinforcement. Another connector 100 having a first device connecting member 18 and a second device connecting member 22, is connected to the pedicle 110 of the adjacent vertebra 90 by another screw 40. The provision of the connectors 14 and 100 on adjacent vertebrae with the rod 30 extending between them creates an artificial facet joint in which limited movement is permitted by the freedom of movement of the pieces of the joint, but which will not permit excessive movement. The action of the artificial facet also mimics the action of the ligaments which surround the spine to limit flexion of the spine.

The rod 30 is secured against excessive movement relative to the connectors 14 and 100 by clamping the rod 30 at some location. Any suitable structure for clamping the rod against movement is possible. There is shown in FIG. 4 a variable angle connector 120 which can be utilized. Such a connector is described in Simonson, U.S. Pat. No. 5,885,285, the disclosure of which is hereby incorporated fully by reference, however, any other suitable clamping or connection device can be utilized. The variable angle connector 120 can be secured to the spine by suitable structure such as another pedicle screw 40. The variable angle connector 120 has a set screw 122 which engages the rod 30 and prevents the rod 30 from moving relative to the variable angle connector 120.

There is shown in FIG. 4 two artificial facet joints. The connectors 14 and 100 with the rod 30 forms one joint. It is also possible to provide an artificial facet joint in which a connector 14 is provided on one adjacent vertebrae, and structure for securing the rod against axial movement relative to the spine is provided on the other adjacent vertebrae. This artificial facet joint would be formed by the connector 100 and structure for securing such as variable angle connector 120, but could be without any other connector such as connector 14. The rod 30 is thereby fixed on one side of the joint, and can slide through the connector 100 on the other side of the joint.

Figure 5:
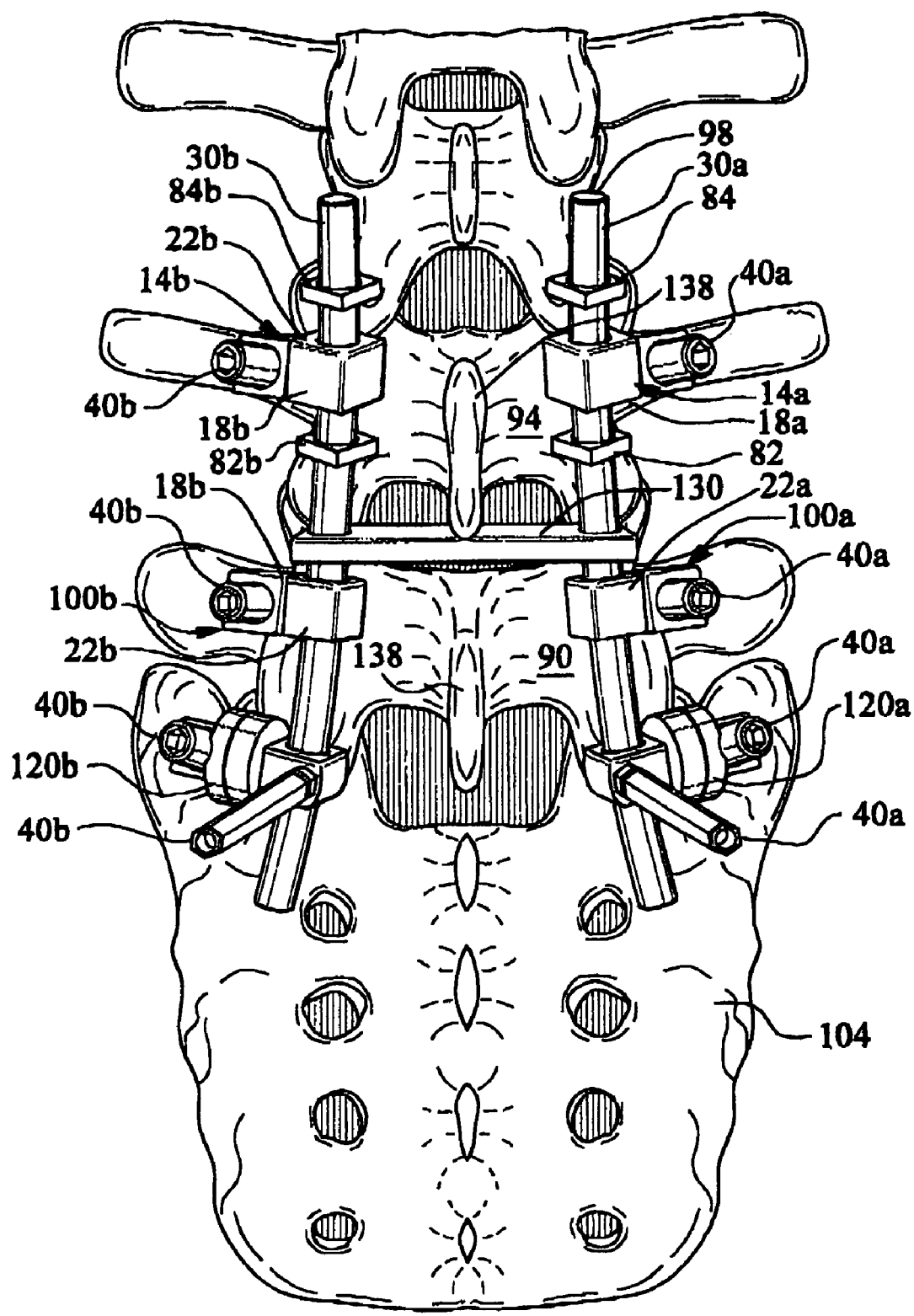
FIG. 5 is a posterior view.

An artificial facet joint is created on each lateral side of the spine, as shown in FIG. 5. There is shown another assembly with spinal rod 30*b* slideably engaged to connectors 14*b* and 100*b*, which are comprised of first device connecting member 18*b* and second device connecting member 22*b*, and are also slideably engaged to screws 40*b*. Variable angle connector 120*b* or other suitable structure is utilized to secure the rod 30B in position.

A transverse member 130 is engaged to rods 30*a* and 30*b*. The transverse member 130 can have apertures which slideably engage the rods 30*a* and 30*b*. In at least one embodiment, the transverse member 130 may be elastic. Other connection means are possible. The transverse connecter may connected to the screws 40*a* and 40*b* themselves to avoid rotation of the bone screws. The transverse member 130 can be in the form of a plate as shown or in any other suitable shape. The transverse member 130 provides torsional stability between the lateral sides of the artificial facet joint. The transverse member can be located between the spinous process 138 of the adjacent vertebrae 90 and 94.

The invention is made of suitable material such as surgical grade stainless steel. Any bio-compatible material with suitable strength can be utilized. The tolerances of the artificial facet joint can be created by variously sizing the rod 30, the screws 40, and the relative size of the apertures. Similarly, the transverse member 130 can be provided with apertures which permit a certain amount of movement. The amount of movement that will be appropriate will depend on the patient, the condition that is being treated, and the location in the spine where the artificial facet joint is located. Some portions of the spine are optimally more flexible than others. The connecting members could be differently dimensioned to provide different strength/flexibility characteristics. The connectors can also be variously sized to accommodate different implantation situations. Connectors can have different sizes to provide different rod to screw distances in the artificial joint. Also, connectors with adjustable distances between the first device connecting member and the second device connecting member can be provided, such as with a threaded connection which can be used to move the two members closer or farther apart.

Figure 6:
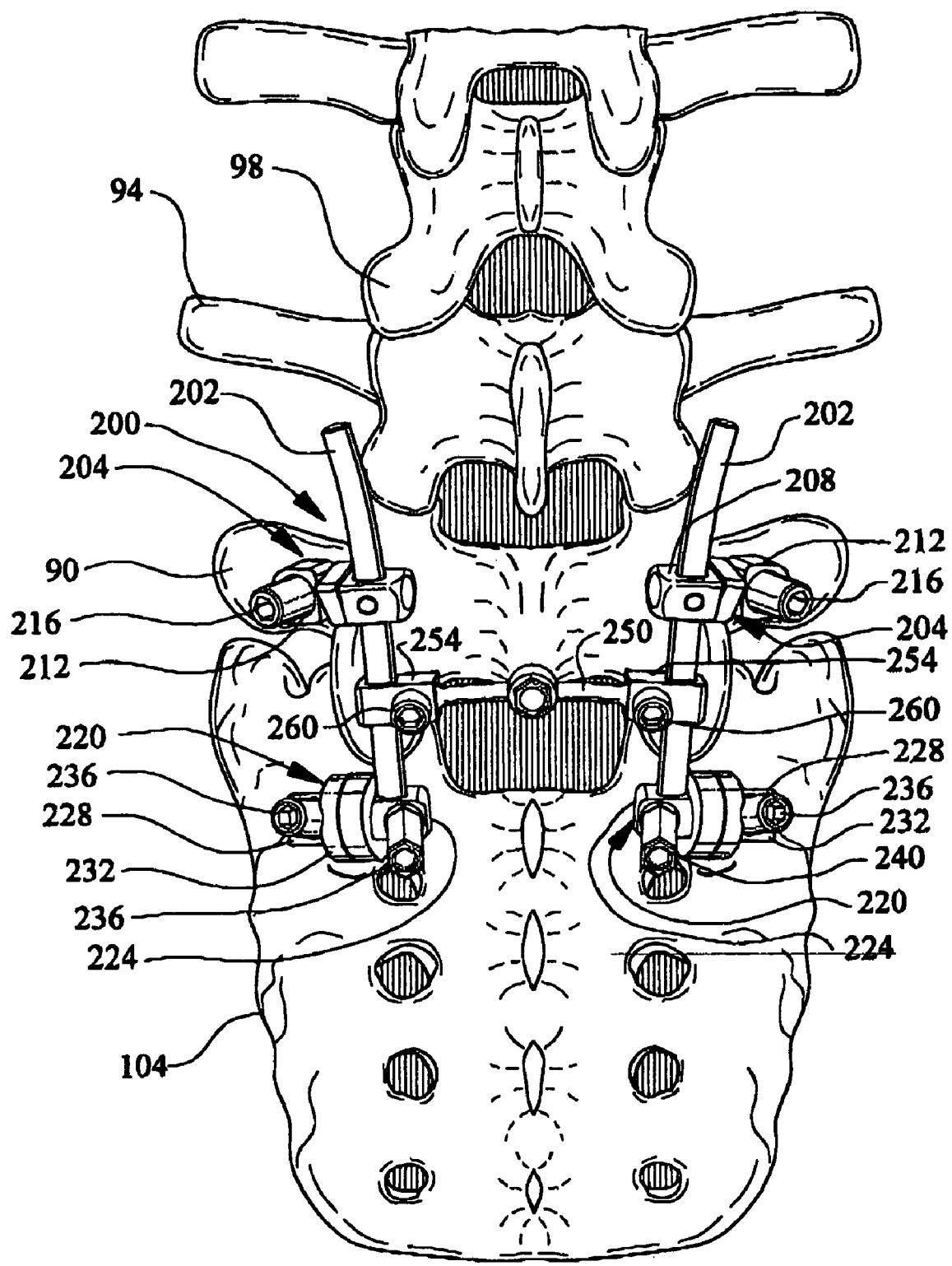
FIG. 6 is a plan view of an alternative embodiment.
Figure 7:
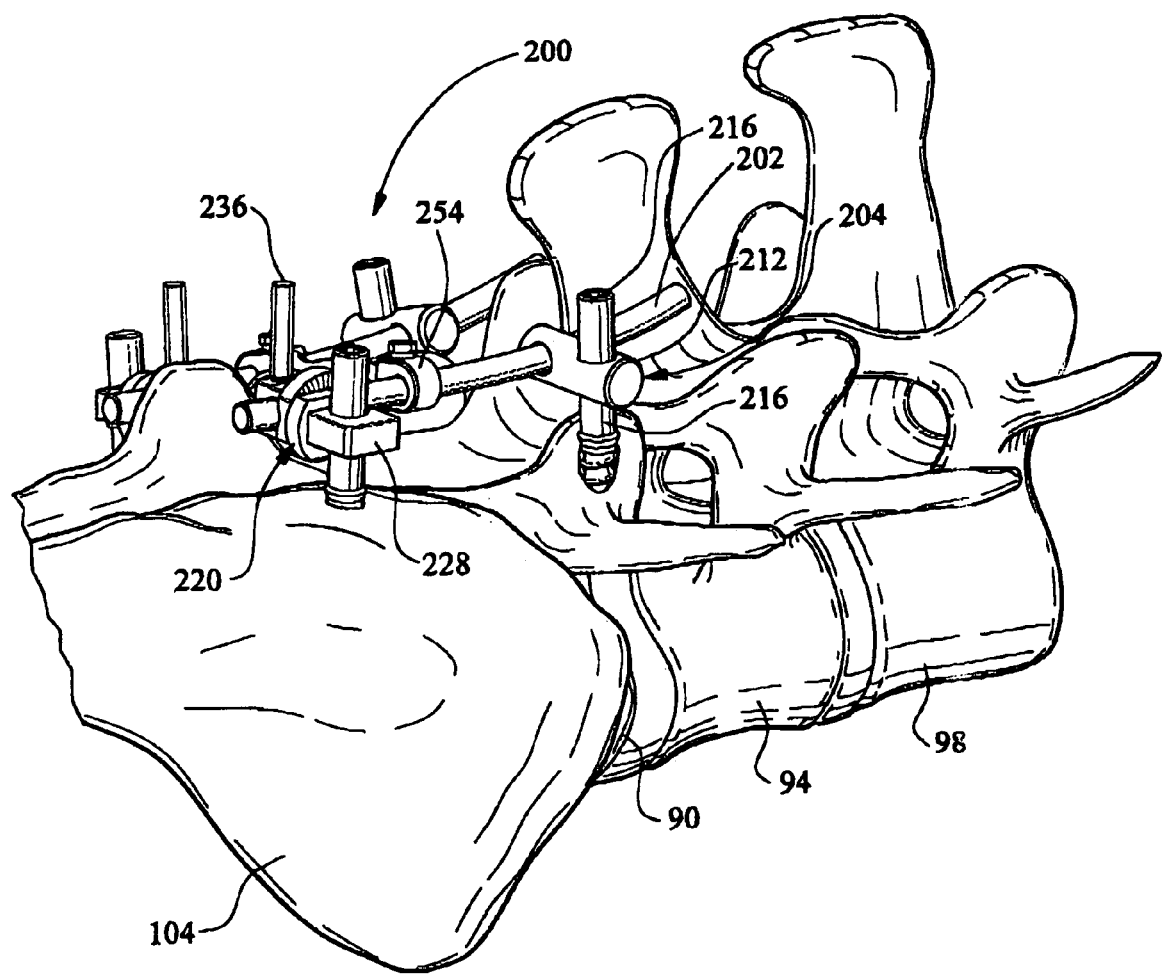
FIG. 7 is a side elevation.

There is shown in FIGS. 6–7 an artificial facet joint 200 having spinal implant rods 202. Sliding connectors 204 engage the rods 202 and permit sliding movement therebetween. Each connector 204 can be constructed to enable pivoting movement of the rod 202 relative to the connector 204. The connectors 204 can have a first connecting member 208 for engaging the rods 202 and a second connecting member 212 for engaging screws 216. The first connecting member 208 is pivotable relative to the second connecting member 212.

Fixation connectors 220 engage the rods 202 to prevent sliding movement therebetween. The fixation connectors can include a first connecting member 224 for engaging the rod 202 and a second connecting member 228 for engaging associated screws 236. The fixation connectors can include interengagement structure 232 for locking the position of the first connecting member 224 relative to the second connecting member 228, and thereby the rod 202 with respect to the screw 236. The rod 202 can be secured substantially parallel to the long axis of the spinal column.

A transverse cross-linking member 250 can be provided to connect the rods 202 and provide the joint with greater stability. End portions 254 can engage rods 202 to permit sliding movement of the transverse member 250 relative to the rods 202. Suitable structure such as set screws 260 can alternatively be used to secure the transverse member 250 in a desired position on the rods 202. The transverse member 250 can be positioned to engage the connectors 204 to limit the range of sliding movement of the rods 202 relative to the connectors 204. The transverse cross-linking member 250 can be made of a material such as an elastic material so as to provide progressive resistance to changes in the distance between the rods 202.

Figure 8:
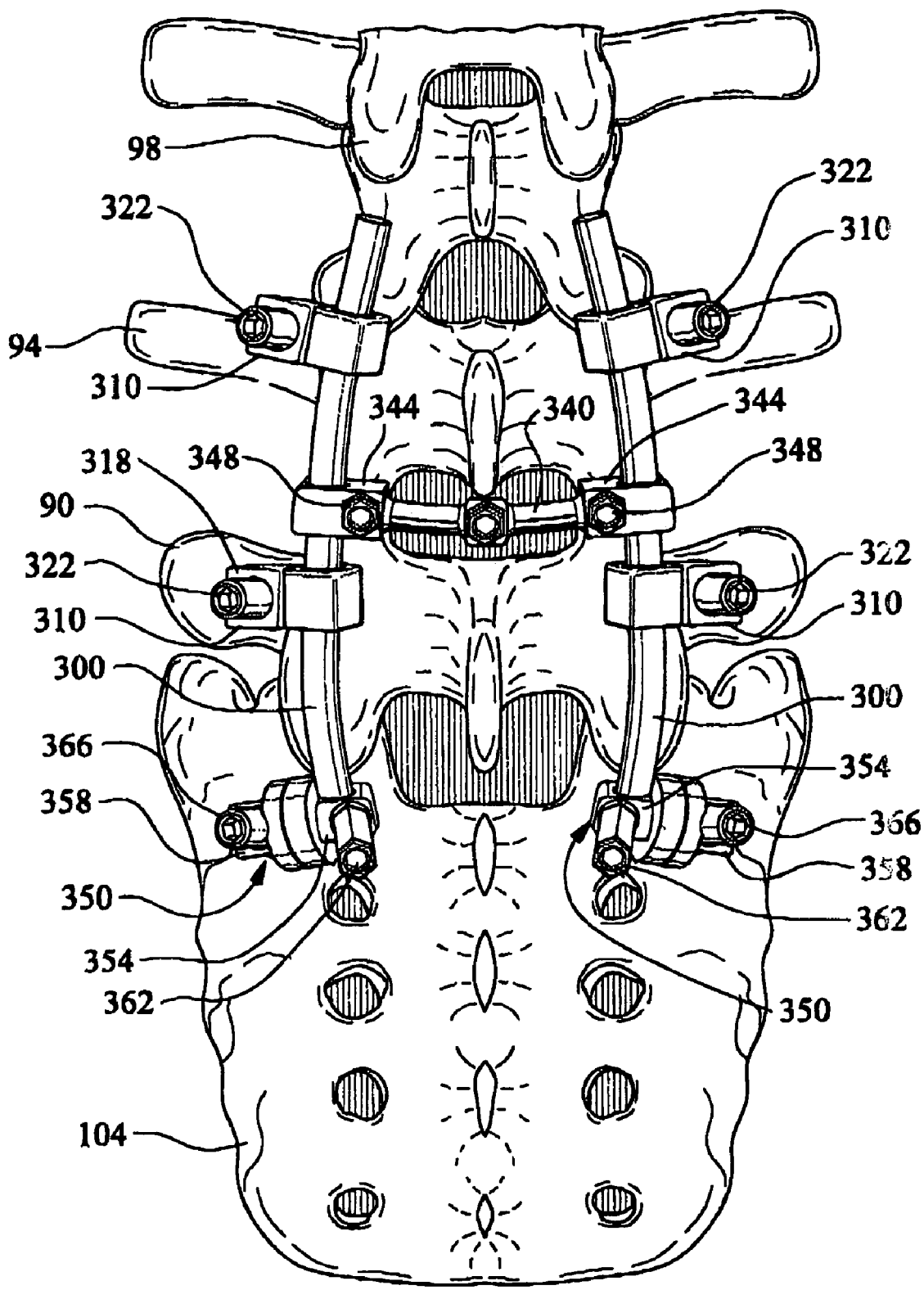
FIG. 8 is a plan view of yet another embodiment.
Figure 9:
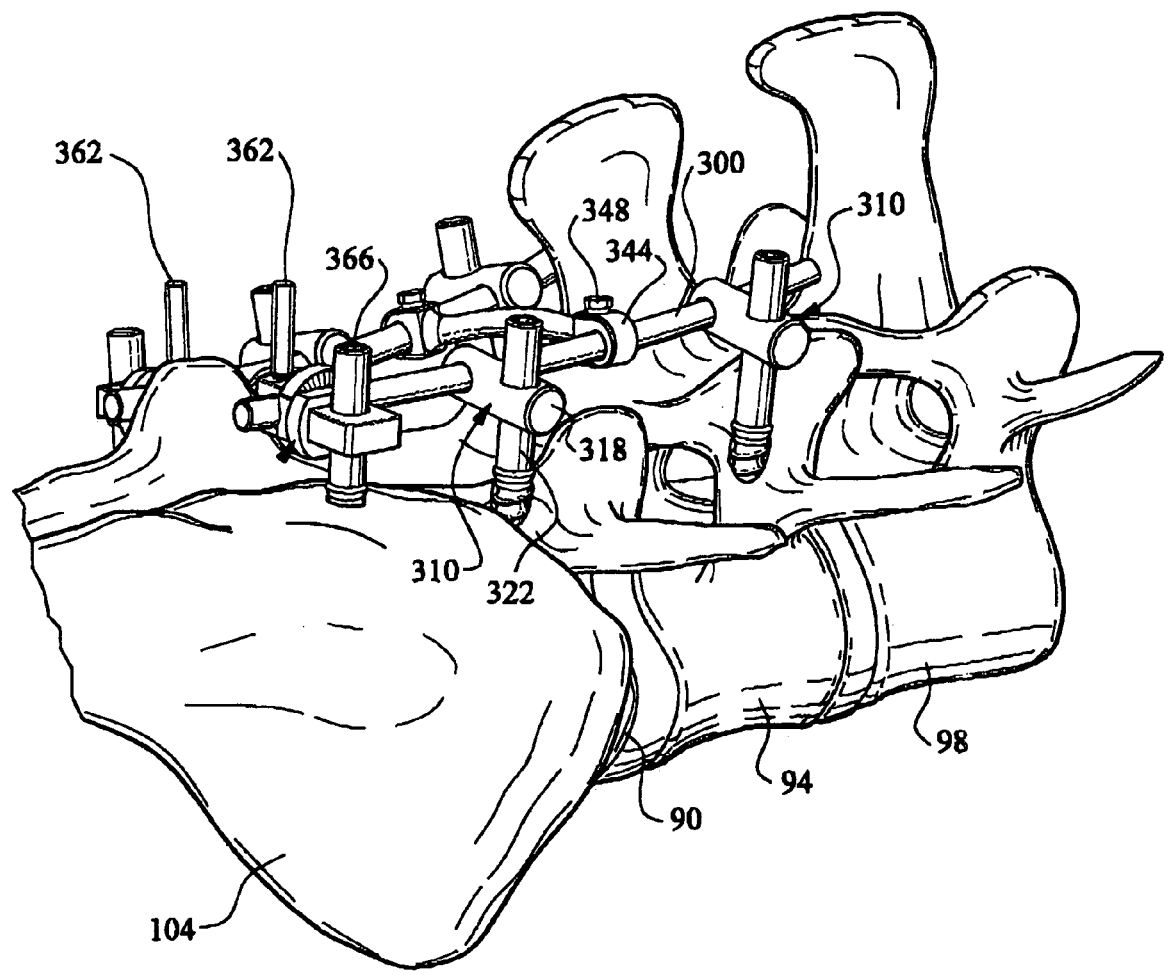
FIG. 9 is a side elevation.

Another embodiment of an artificial facet joint is shown in FIGS. 8–9. The artificial facet joint includes rods 300 engaged by sliding connectors 310. The connectors 310 can have a first device connecting member 314 for engaging the rods 300 and second device connecting members 318 for engaging screws 322. The connectors 310 are secured to the vertebrae 90, 94 by the screws 322. The first device connecting members 314 engage the rods 300 so as to permit sliding movement of the rods 300 relative to the first device connecting members 314. The first device connecting members 314 pivot relative to the second device connecting members 318 to permit pivoting of the rods 300 relative to the screws 322.

Fixation connectors 350 secure the rods 300. A rod connecting member 354 can have suitable structure for engaging the rod 300 such as set screw 362. A screw connecting member 358 engages the screw 366. The screw connecting member 358 is pivotable relative to the rod connecting member 354. The rods 300 are thereby pivotable in the sagittal plane.

A transverse cross-linking member 340 can be provided and secured between the rods 300 to provide stability to the joint. Ends 344 can be joined to the rods 300 so as to permit sliding movement, or suitable structure such as set screws 348 can be provided to prevent sliding movement. The transverse member 340 can be positioned on the rods 300 so as to contact connecting members 310 to prevent excessive movement of the rods 300 relative to the connectors 310. The rods 300 can span three or more vertebrae as the implantation may require.

Figure 10:
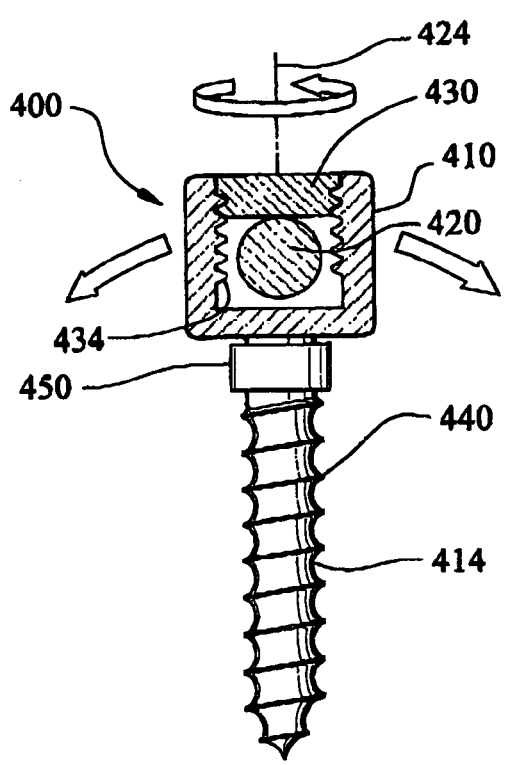
FIG. 10 is front elevation of still another embodiment.
Figure 11:
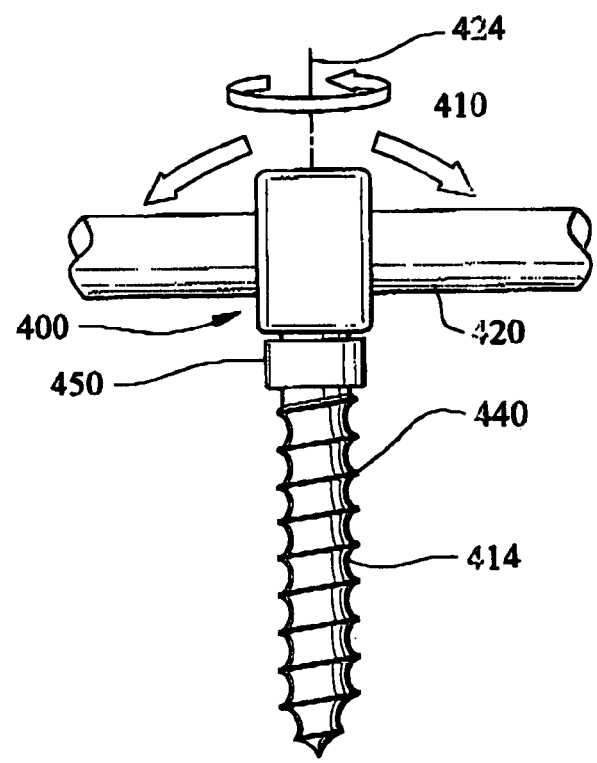
FIG. 11 a side elevation.
Figure 12:
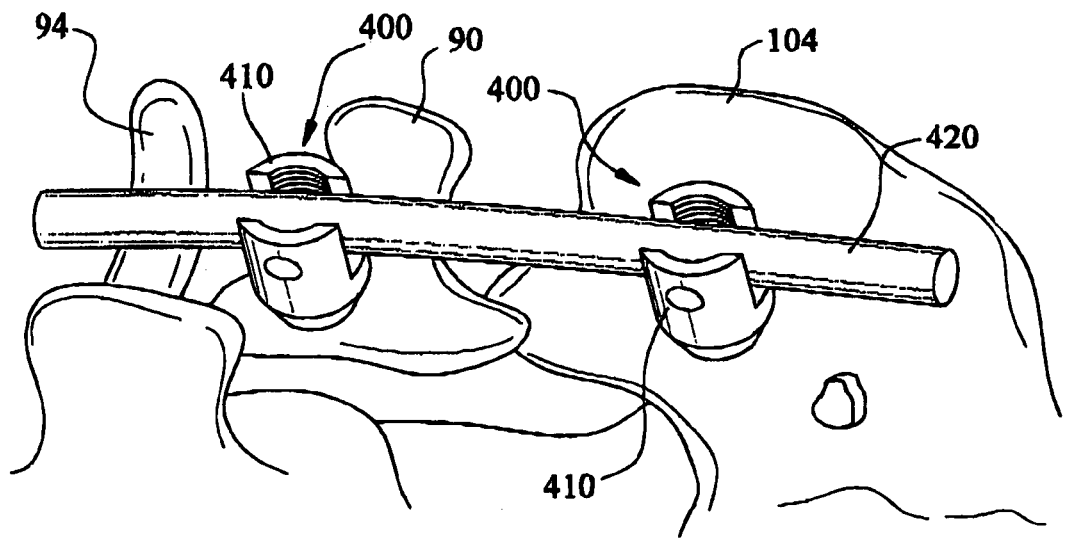
FIG. 12 is a perspective view as implanted in a spine.

There is shown in FIGS. 10–12 an alternative connector for an artificial facet joint according to an alternative embodiment of the invention. The connector 400 has a head portion 410 and a screw portion 414. The head portion 410 is capable of sliding engagement of a spinal rod 420. The head portion 410 is pivotally connected to the screw portion 414. The head portion 410 can be polyaxially pivotable with respect to the screw portion, such that the head portion can pivot with respect to the longitudinal axis 424 of the screw portion 414 as shown by the arrows in FIGS. 10–11. The pivoting connection can be provided by any suitable structure, such as a ball-and-socket joint. Also, the head portion 410 can be joined to the screw portion 414 to permit rotation of the head portion 410 about the longitudinal axis 424 as shown. Further, the head portion 410 can be detachably connected to the screw portion 414 by the provision of removable engagement structure such as a nut which engages a post on the screw portion 414. The rod can be of any suitable shape. In one embodiment, the rod can be a plate with a groove through which extends the polyaxially pivotable screws.

The head portion 410 can have any suitable structure for engaging the rod 420. In the embodiment shown in FIGS. 10–12, the head portion 410 has a cup or saddle shape for receiving the rod 420. A cap 430 can be engaged to the head portion by suitable structure such as threads 434 to secure the rod 420 within the head portion 410. Threads 440 on the screw portion 414 can be provided to engage the screw portion 414 to the vertebrae.

The degree of angulation of the head portion 410 with respect to the longitudinal axis 424 of the screw portion 414 can be limited by suitable structure such as a stop 450. As the head portion 410 pivots with respect to the screw portion 414, the head portion will contact the stop 450 to prevent or retard further pivoting. The stop can be integral with the screw portion 414 or attached to the screw portion 414 by suitable means such as welding, adhesives, or set screws. The resistance provided by the stop 450 can be progressive such that increased angulation of the head portion 410 with respect to the screw portion 414 will result in increased resistance. The stop 450 can be made of an elastic material which will provide increased resistance as contact with the head portion 410 increases the compression of the elastic material. It is alternatively possible to limit pivoting movement of the head portion 410 with respect to the screw portion 414 by other structure, such as projections on the head portion 410 which contacts the stop 450, or cooperating structure on the screw portion 414 or the rod 420. Further, elastic material can be provided on the rod, such as in the form of an tube that is fitted over the rod 420, to contact the connector and limit the motion of the artificial facet joint.

The implantation of the connectors 400 is shown in FIG. 12. The screw portion 414 is engaged to the vertebrae 90 and/or sacrum 104. The rod 420 is positioned in the channels of the head portions 410. The caps 430 can then be secured to the head portions 410 to secure the rod 420 in place. Suitable clamping structure can be provided to secure the rod 420 against sliding movement. The caps 430 can be tightened to clamp the rod 420, or can form a channel for permitting sliding movement. A connector 410 at the lowermost vertebrae or the sacrum can be used to clamp the rod 420, while connectors 410 that are secured to upper vertebrae can permit sliding movement to permit the spinal column to move within the limits of the artificial facet joint. The connectors 410 and rod 420 can all be implanted through percutaneous incisions.

The spinal implant rods used in the artificial facet joints of the invention can be of any suitable construction, shape, material and length. The rods can be bent in a shape which will essentially guide the connectors in sliding movement along the rod. The spine will thereby be directed by the rod to flex according to a path and limits that are determined to be best suited for the particular patient. The connectors can have a fixed angle relative to the rod connecting portions and screw connecting portions, or can have structure which will limit the angulation, to provide that the connectors follow the spinal rod according to the desired path. The screws can be angled or shaped so as to provide a guide path for bending of the spine. A barrier device can be provided in a suitable form such as a plastic cover to reduce the contact between the artificial facet joint and surrounding tissue.

Figure 39:
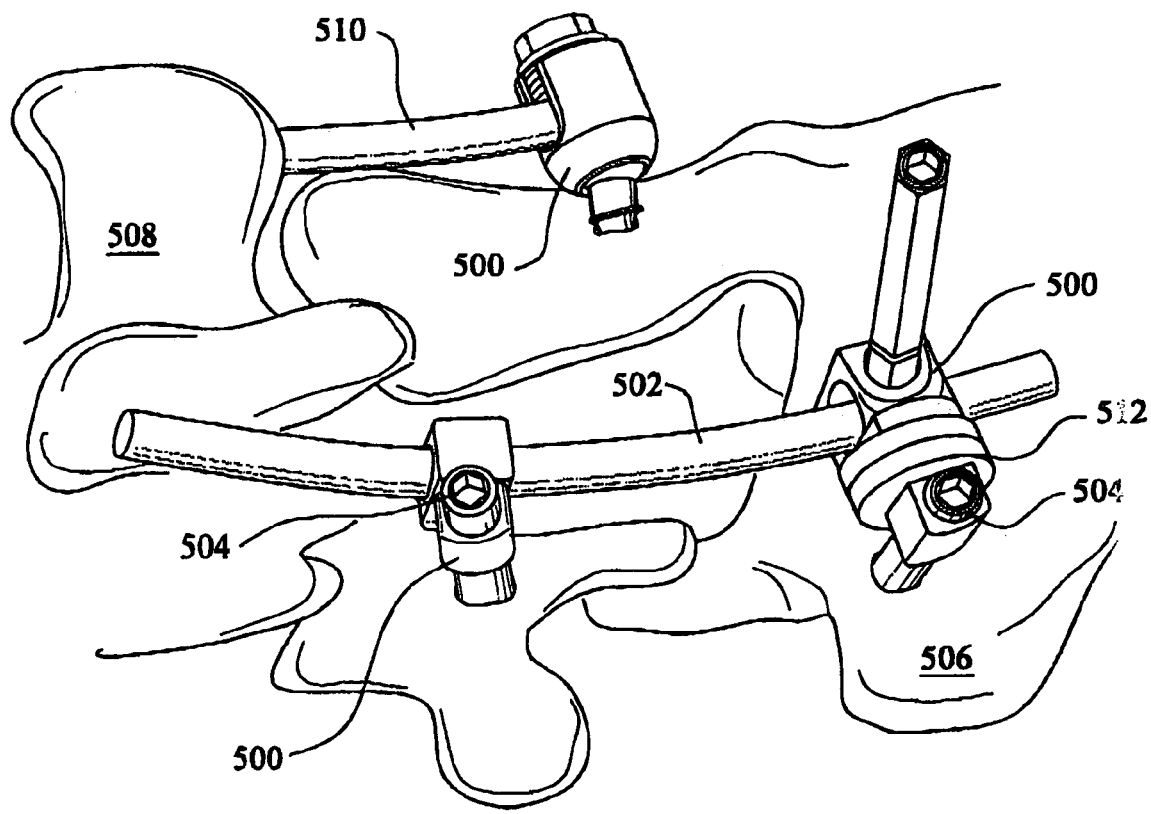
FIG. 39 is a perspective view of a facet joint supported by a connection system of this invention.
Figure 40:
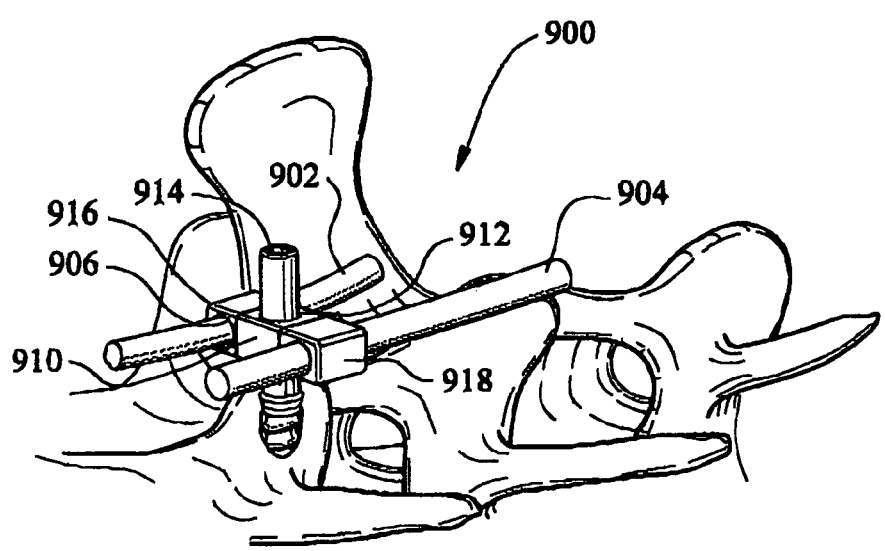
FIG. 40 is a perspective view of a compound connector usable to receive at least two rods.
Figure 41:
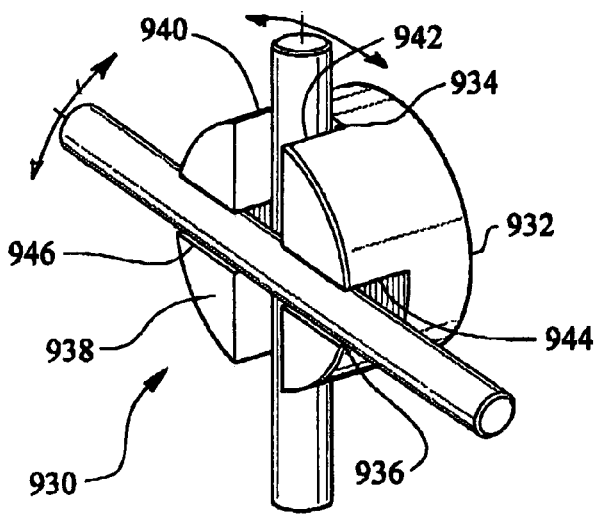
FIG. 41 is a perspective view of an alternative connector.

In yet another embodiment of this invention, as shown in FIG. 39, any connector 500 may be used to stabilize a facet joint such that the connectors 500 enable a rod 502 to be coupled to a post 504 and any connector 512 may be used to slideably couple the rod 502 to other vertebrae. The post 504 may be fixedly coupled to vertebrae, which may be a sacrum 506 or any other vertebrae 508 forming a spine. The post 504 may be attached using a mechanical connector, such as, but not limited to, a screw or a hook; an adhesive; or other appropriate material compatible with the human body. The connector 500 may be attached to the post 504 at a point above the vertebrae. Thus, the connector 500, and those shown in FIGS. 13–35 and 40–44, do not rely on tightening the connector 500 against the vertebrae. Rather, the connector 500 may be tightened to the post 504 at a point above the vertebrae, which enables the connector 500 to be tightened more than if the connector 500 were only tightened against a vertebrae. The connector 500 may be tightened to a post using a set screw, a screw, a bolt, a bolt inserted into the connector 500 or other appropriate device.

In at least one embodiment, a rod 510 may be coupled to an adjacent vertebrae. However, in other embodiments, the rod 510 may be coupled to vertebrae that are not directly adjacent to each other. The rod 510 may have any one of numerous configurations for coupling vertebrae together. In at least one embodiment, the rod 510 may have a generally cylindrical cross-section enabling the rod 510 to pass through cylindrical apertures in the connectors 500 and 512 and enable the rod 510 to rotate within the aperture about a longitudinal axis of the rod 510. In addition, the rod 510 may have other cross-sections that enable the rod 510 to rotate within the connectors 500 and 512. The rod 510 may have sufficient strength to resist bending under loads generated by movement of the spine to which the rod 510 is coupled or may be configured to bend when loaded with a force. In at least one embodiment, a rod 510 made of a biocompatible metal or composite material may be sized such that the rod occupies relatively little space when installed in a patient yet possesses the necessary strength to stabilize the facet joint of the patient. In yet another embodiment, the rod 510 may be formed from a material that is flexible during installation of the rod into a patient but becomes rigid post-operatively.

As shown in FIGS. 13–38, connectors for aligning a rod with a spine may come in numerous designs. This invention is directed to connectors, which may be referred to as spinal stabilization devices, enabling a rod to slideably pass through the connector. In at least one embodiment, the connectors cooperate such that one of the connectors is fixedly coupled to the rod while the remaining connectors on the rod allow the rod to slide back and forth through the connector. Thus, the rod allows movement generally along its longitudinal axis but prevents movement of the connector generally orthogonal to the rod. When installed in a patient, the connectors enable movement of a spine in the sagittal plane but restricts movement in the coronal and transverse planes.

In other embodiments, movement of two vertebrae may be controlled by attaching a first rod to a first vertebrae and a second rod to a second vertebrae. The first and second rods may be coupled together so that at least one of the rods may move relative to the other rod generally along a longitudinal axis of the rods. In at least one embodiment, the first and second rods may be coupled together using a connector in a slideable relationship enabling the first and second rods to move relative to each other. The connector may be positioned between a point at which a first rod is coupled to a first vertebrae and a point at which a second rod is coupled to a second vertebrae. In addition, use of the transverse cross-linking member 130, 250, 340 as shown in FIGS. 5, 6, and 8, limits movement of the rod assembly orthogonal to the longitudinal axis of the assembly. Thus, the configuration of rods, posts, and connectors, limits movement of a spine to a defined range of motion correlating to a range of motion allowed by a facet joint. In general, these connectors allow limited motion of a spine in the sagittal plane post-operatively and restrict movement in the coronal and transverse planes.

Figure 35:
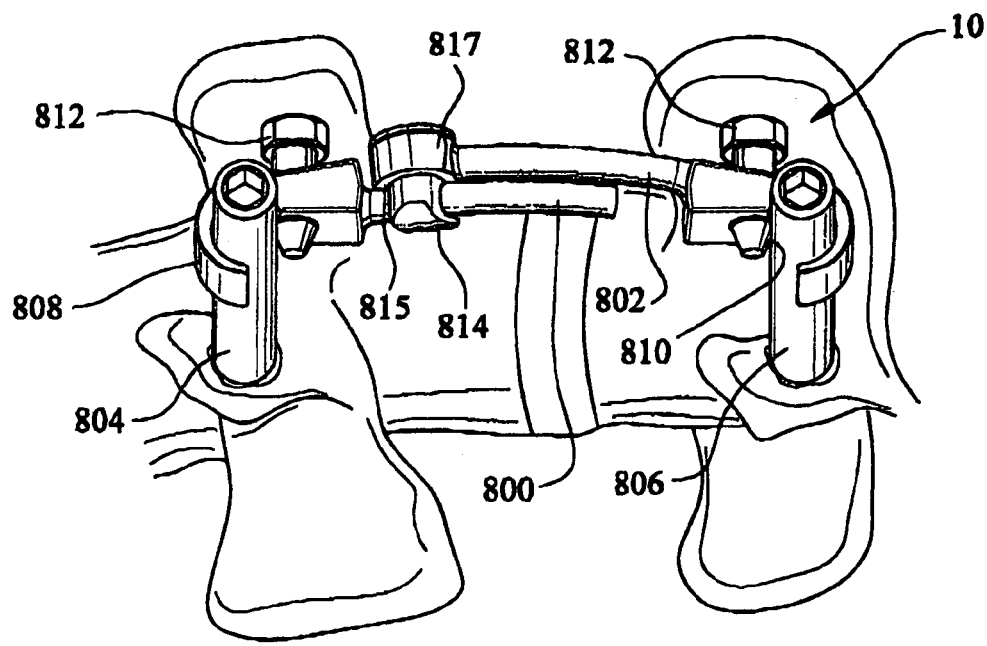
FIG. 35 is a perspective view of another alternative connector.
Figure 36:
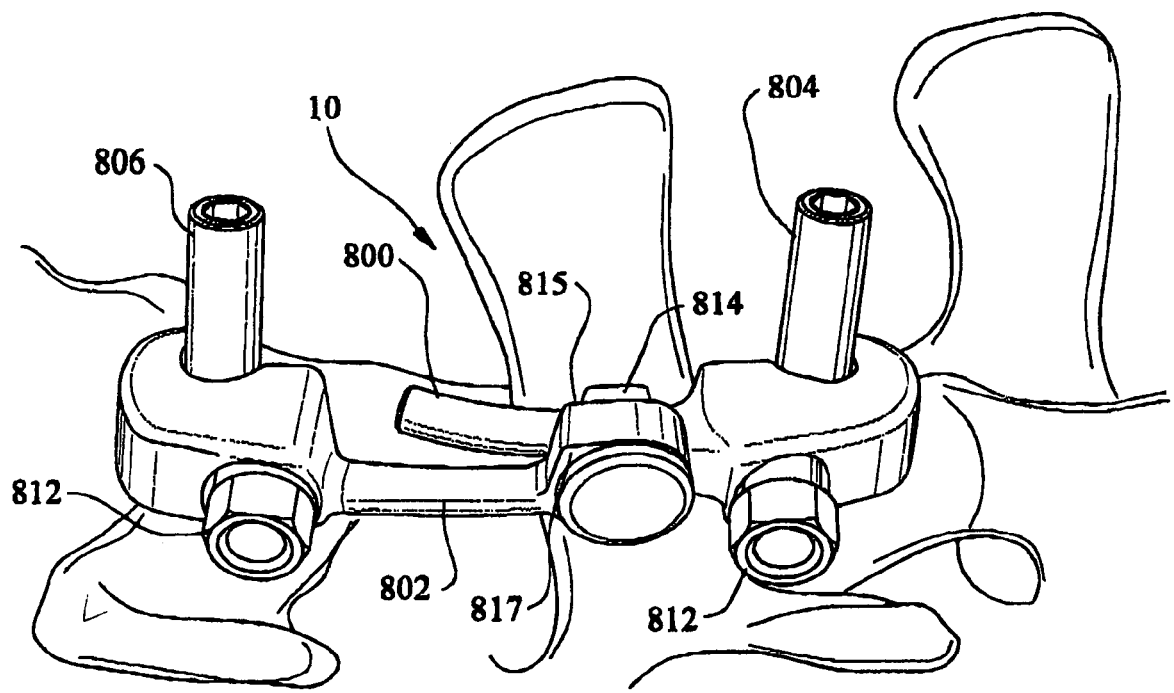
FIG. 36 is a perspective view of the alternative connector shown in FIG. 35.

For instance, FIGS. 35 and 36 show a connector assembly 10 formed from a connector 810 having a first aperture 801 slideably receiving a first rod 800 coupled to a first vertebrae and having a second aperture 803 receiving a second rod 804 coupled to a second vertebrae. The first rod 800 may be adapted to form a slideable connection with the connector 810 in the first aperture 801. The connector 810 is adapted to be suspended by the first and second rods 800, 802 between the first and second vertebrae and to maintain the slideable connection between the first aperture 801 and the connector 810 post-operatively.

More specifically, FIG. 35 shows two rods 800, 802 that are slideably coupled together. The rods 800, 802 may be fixedly attached to posts 804, 806, respectively. Alternatively, one of the rods 800, 802 may slideably attached to a post 804 or 806 such that the rod 800 or 802 may slide generally along a longitudinal axis of the rod 800, 802. In addition, one or more of the rods 800 or 802 may be coupled to a post 804, 806 such that the rod 800 or 802 may move vertically along the length of the post 804, 806.

The posts 804, 806 may include a threaded portion, a hook, or other device for attaching the posts 804 and 806 to a vertebrae or a sacrum. The rods 800, 802 may include apertures 808, 810 for attaching the rods 800, 802 to the posts 804, 806. The rods 800, 802 may include a tightening device 812, such as a bolt or other appropriate device, for tightening the rods 800 and 802 to the posts 804, 806, respectively. A connector 814, which may be referred to as a slider, may slideably couple rod 800 to rod 802. The connector 814 may be fixedly coupled to rod 802 and may be slideably coupled to rod 802, or vice versa. In at least one embodiment, the connector 814 may include a first aperture 815 for receiving a first rod 800 and a second aperture 817 for receiving a second rod 802. Such a connection enables limited movement of adjacent vertebrae relative to each other. The rods 800, 802 may have generally cylindrical cross-sections or other cross-sections enabling the rods 800, 802 to slide relative to each other in the connector 814.

Figure 37:
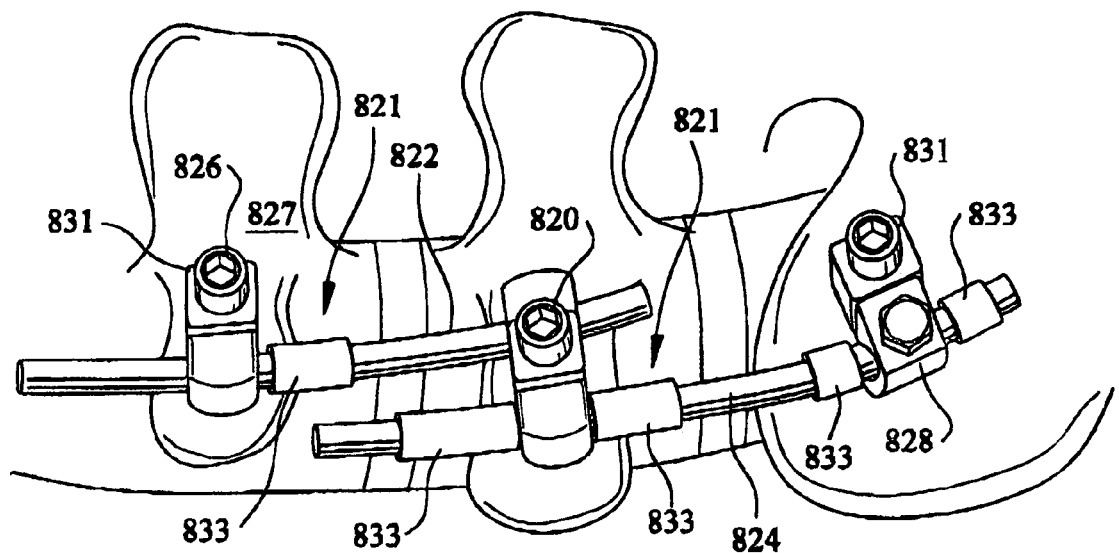
FIG. 37 is a perspective view of yet another alternative connector.
Figure 38:
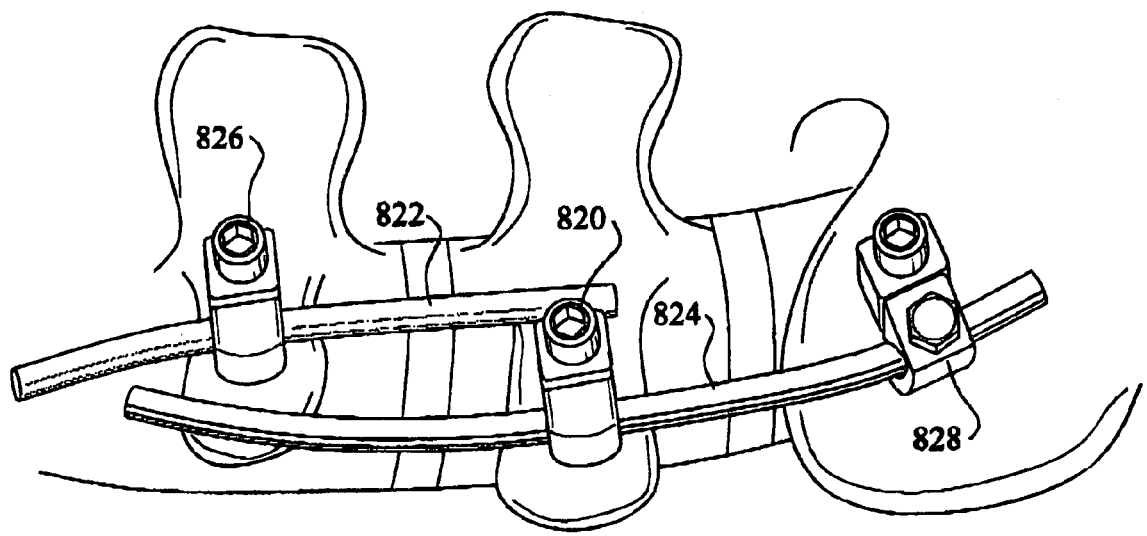
FIG. 38 is a perspective view of the alternative connector shown in FIG. 37.

FIGS. 37 and 38 show a connector 820 usable to couple two rods 822, 824 together. The connector 820 may be used to connect two rods 822, 824 together along the lengths of the rods and not at a post 826, 828. Rather, the connector 820 may be used to couple the rods 822, 824 together between the posts 826, 828. The rods 822, 824 may be fixedly attached to the posts 826, 828, or may be slidably attached to the posts 826, 828 such that the rods 822, 824 may move vertically along the posts 826, 828. The connector 820 may be suspended between the posts 826 and 828. The connector 820 may be slideably attached to each rod 822, 824 or may be slideably attached to rod 822 and fixedly attached to rod 824, or vice versa. The connector 820 may include a first aperture 821 for receiving a first rod 822 and a second aperture 823 for receiving a second rod 824. The connector 820 enables the rods 822, 824 to move generally parallel to each other or, in other words, generally along the longitudinal axes of the rods 822, 824. The connector 820 may have any configuration for enabling movement between rods 822, 824 in the sagittal plane, but with only limited movement in the coronal and transverse planes.

Movement limiting devices 831, 833 may be coupled to the rods 822, 824 on either side of the connector 820 to limit the amount of movement a rod 822, 824 may undergo relative to the connector 820. The movement limiting devices 831, 833 are not limited to any particular configuration. However, in at least one embodiment, the movement limited devices 831, 833 are formed from an elastic material.

The connection devices shown in FIGS. 13–34 and 40–44 may be used in the assemblies shown in FIGS. 35-38 to stabilize a facet joint in a patient's spine. A first rod 822 may be secured to a first vertebrae 827 in a manner that substantially prevents movement of the first rod 822 relative to the first vertebrae 827. A second rod 824 may be coupled to a second vertebrae 829 in a manner that substantially prevents movement of the second rod 824 relative to the second vertebrae 829. The first and second rods 822, 824 may be slidably coupled together at a connector 820 positioned between a first point 831 where the first rod 822 is coupled to the first vertebrae 827 and a second point 833 where the second rod 824 is coupled to the second vertebrae 829. At least one of the first and second rods 822, 824 remain in a slideable relationship with the connector post-operatively to enable the patient to move the spine.

Portions of the rods 822, 824 may be inserted into apertures 821, 823 in the connector 820 forming slidable connections. In at least one embodiment, one of the slidable connections may be a fixed connection. In another embodiment, a second spinal joint stabilization device may be coupled to another side of a facet or laterally displaced from the first spinal stabilization device. The spinal joint stabilization device may be have a connector positioned between posts connected to vertebrae or may have slidable connections at the posts enabling adjacent vertebrae to move relative to each other.

In at least one embodiment, as shown in FIG. 37, the spinal joint stabilization device 821 may be used in series with each other to support two or more vertebrae. The joint stabilization device 821 may be coupled to three vertebrae, each adjacent to each other or separated from each other. Two or more spinal joint stabilization devices 821 may be coupled together in series to cooperate to stabilize a portion of a patient's spine. One or more of the joint stabilization devices 821 may include a rod, such as 822, 824, slideably engaged to a post, 820, 826, or 828, which is attached to a vertebrae. All or a portion of the series of joint stabilization devices 821 may include slideable connections between a rod and a post. In alternative embodiments, one or more of the stabilization devices may use the connector 814 shown in FIGS. 35 and 36 where the connector 814 is suspended by two rods 800, 802 between adjacent posts 804, 806.

A series of joint stabilization devices 821 may be connected together using connectors shown in FIGS. 1–34 and 40–44. Alternatively, the connector 900 shown in FIG. 40 may be used to couple adjacent rods 902 and 904 together using a single compound connector having apertures 906 and 908 for receiving rods 902 and 904 respectively. The connector 900 may be formed from a body 910 having an aperture 912 for receiving a post 914. The connection between body 910 and post 914 may or may not be slideable. In at least one embodiment, ends 916 and 918 containing apertures 906 and 908 may rotate relative to the body 910 or may not rotate. In addition, the body 910 may or may not slide on the post 914.

Figure 13:
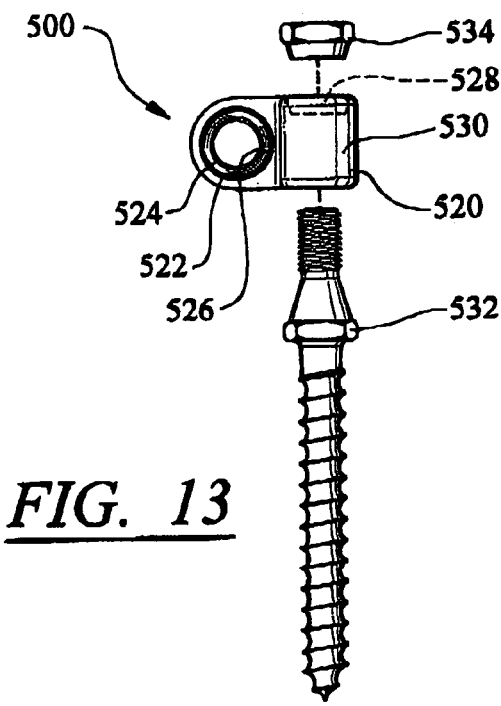
FIG. 13 is an exploded perspective view of an alternative connector.
Figure 14:
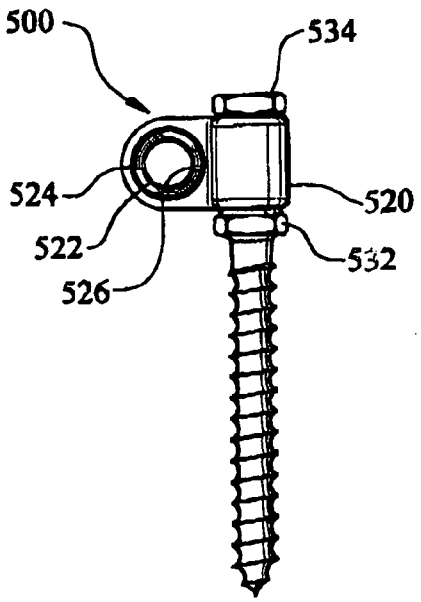
FIG. 14 is an assembled perspective view of the connector shown in FIG. 13.

FIGS. 13–44 display alternative embodiments of connectors for attaching a rod to a vertebrae while also allowing the rod to slide relative to the connector. As shown in FIGS. 13 and 14, connector 500 may be formed from a body 520 configured to contain a spherical receiver 522 having an aperture 524 for receiving a rod. In at least one embodiment, the body 520 is a rigid member forming a body of the connector 500. The spherical receiver 522 may include at least one slot 526 enabling the diameter of the aperture 524 to be reduced. The body 520 may contain two apertures 528, 530 for receiving a post 532, such as, but not limited to, a screw, a hook, or other appropriate device. A rod may be slideably contained by the connector 500 by passing the rod through the aperture 524. In at least one embodiment, the nut 534 may be tightened to secure the body 520 to a screw 532 without clamping the connector 500 to a rod passing through the aperture 524. Instead, the rod is allowed to slide freely through the aperture 524. Thus, the connector 500 may be used to slideably attach a rod to a post to stabilize a facet joint. In addition, the connector 500 enables a rod to rotate through a limited range of motion about an axis generally orthogonal to the longitudinal axis of the rod. Such movement enables the connector 500 to be used to strengthen a facet joint while allowing the facet joint to move through its natural range of motion. Thus, the connector 500 may be used to create a movable facet joint.

Figure 15:
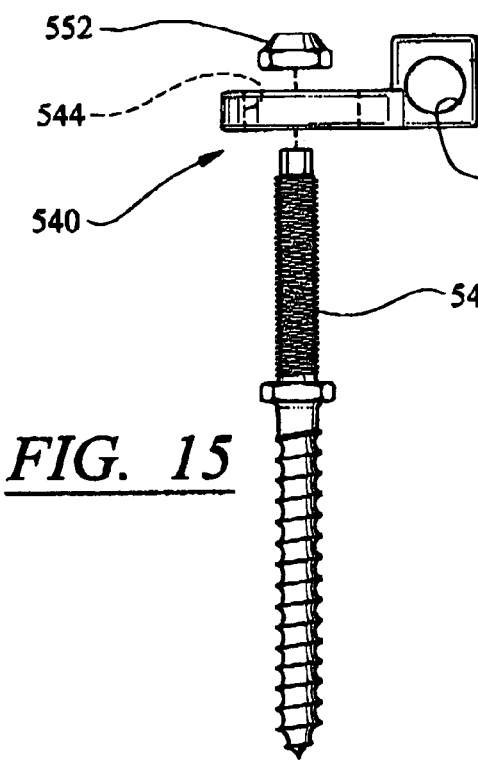
FIG. 15 is an exploded perspective view of another alternative connector.
Figure 16:
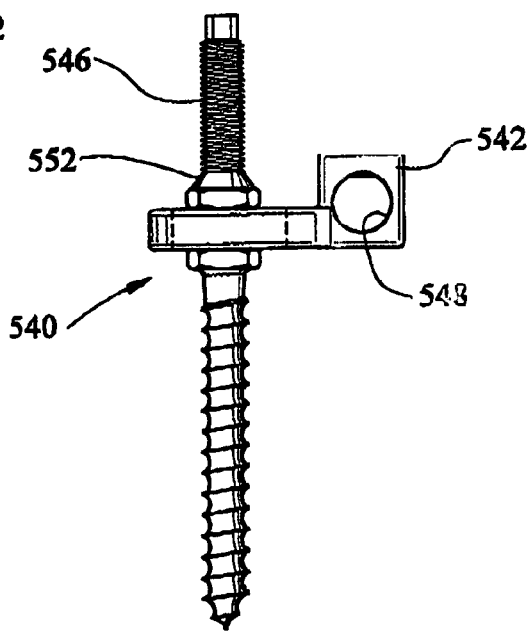
FIG. 16 is an assembled perspective view of the connector shown in FIG. 15.

FIGS. 15 and 16 show another embodiment of a connector 540 used to attach a rod to vertebrae. The connector 540 may be formed from a body 542 having a slot 544 sized to receive a post 546 and a structure 548 for movable engagement of another structure of an artificial facet joint. This structure may be any structure 548 enabling a rod or other connection member to move generally along a spine. In at least one embodiment, the structure 548 may be an aperture 548 for receiving a rod (not shown). A nut 552 may be used to attached the body 542 to the post 546. More specifically, the nut 552 may tighten the body 542 against a stop 543 on the post 546. This configuration enables the body 542 to be securely fastened to the post 546 without relying on body 542 maintaining contact with a vertebral surface.

The rod may slide within the aperture 548 generally parallel to a longitudinal axis of the rod and to restrict movement of the rod generally orthogonal to the longitudinal axis of the rod. This configuration also enables the longitudinal axis of a rod held in aperture 548 to be offset from the longitudinal axis of the post 546. In addition, the body 542 may move medially and laterally relative to the post 546 when the post 546 is inserted in the slot 544.

Figure 17:
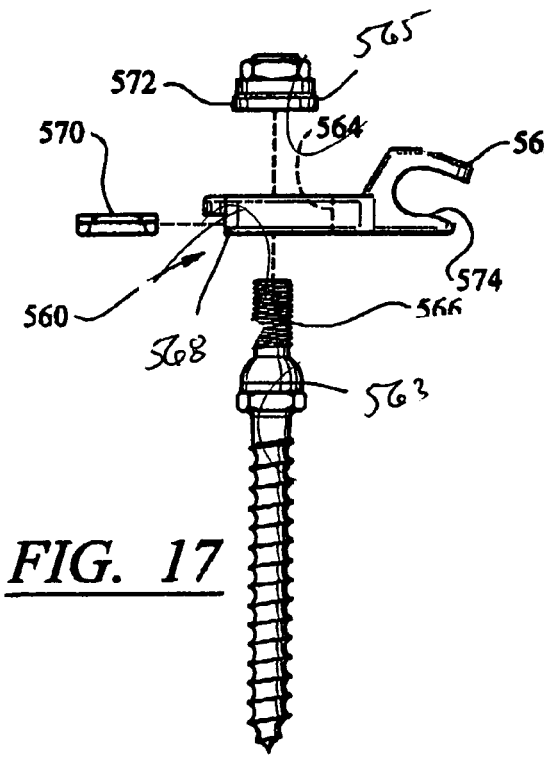
FIG. 17 is an exploded perspective view of yet another alternative connector.
Figure 18:
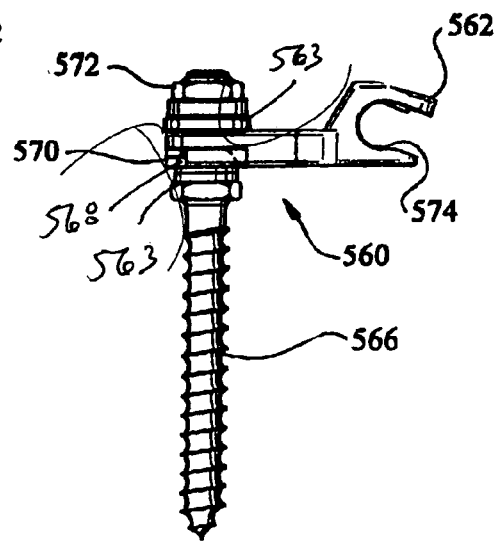
FIG. 18 is an assembled perspective view of the connector shown in FIG. 17.

FIGS. 17 and 18 show a connector 560 having a body 562 with a slot 564 for receiving a post 566, which may be connected to a screw, hook, or other such device. The body 562 may also include grooves 568 for receiving a slider 570 for guiding the post 566 in the slot 564. The slider 570 may move back and forth along the grooves 568. The post 566 may be held in the slot 564 by tightening a nut 572 onto the post 566 or using other tightening devices. The body 562 include a stop 563 usable secure the body 562 to the post 566. The post 566 may include a generally curved outer surface enabling the body to be secured to the post 566 at positions other than orthogonal to a longitudinal axis of the post 566. In addition, a washer 565 may be used to facilitate attaching the body 562 to the post 566 at relationship other than generally orthogonal. In addition, the washer 565 may have a generally curved outer surface upon which the nut 572 may bear.

The body 562 may also include an aperture 574, which may be referred to as a gap, for receiving a rod (not shown). The gap 574 may have a cross-sectional shape having a C-shape such that the gap 574 is capable of retaining a rod.

Figure 19:
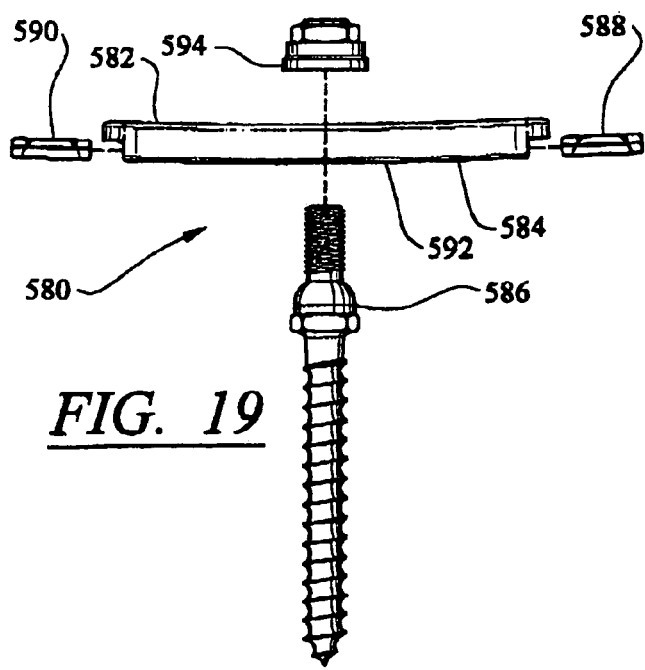
FIG. 19 is an exploded perspective view of another alternative connector.
Figure 20:
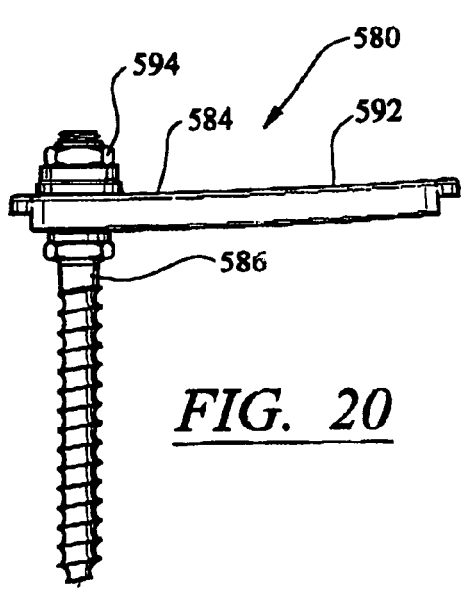
FIG. 20 is an assembled perspective view of the connector shown in FIG. 19.

FIGS. 19 and 20 show a connector 580 formed from a body 582 having a slot 584 for receiving a post 586. The slot 584 enables the post 586 to move horizontally or medially and laterally, in the slot 584. The post 586 may be attached to the body using a nut 594 or other such device. The body 582 also includes two sliders 588, 590. One slider 588 is positioned proximate to the slot 584 for receiving a post for guiding the post 586, and the other slide 590 is capable of receiving an attachment device (not shown) through a slot 592. The attachment device may be configured to hold a rod in a slideable manner allowing the rod to slide relative to the post 586.

Figure 21:
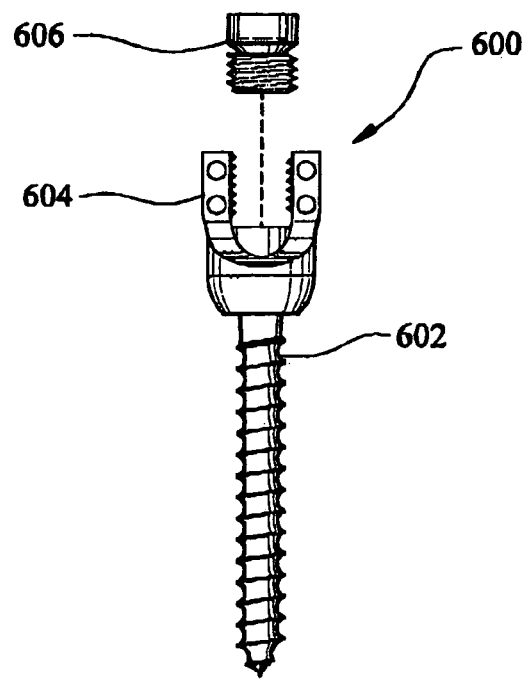
FIG. 21 is an exploded perspective view of still another alternative connector.
Figure 22:
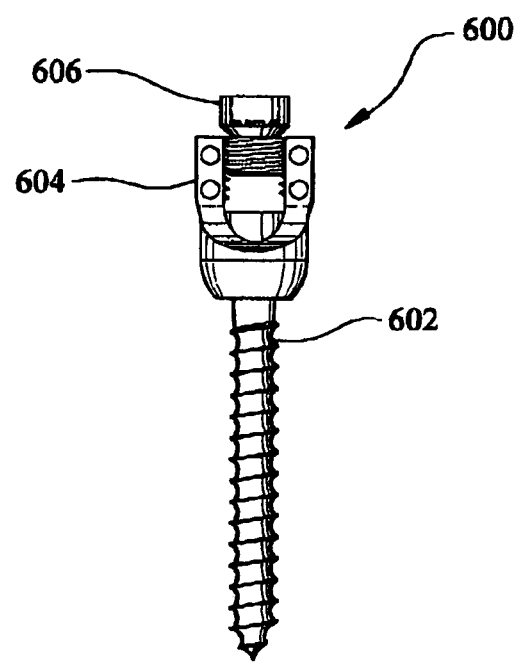
FIG. 22 is an assembled perspective view of the connector shown in FIG. 21.

FIGS. 21 and 22 show a connector 600 having a polyaxial head capable of rotating in numerous directions. A threaded member 606 may be used to keep a rod attached to the connector 600. More specifically, the connector 600 may include a post 602 configured to be attached to a vertebrae of a human. The post 602 may have a hemispherical head enabling a receiver 604 to rotate about at least two axes. The receiver 604 may be adjusted to rotate during installation- and post operatively in a patient. The receiver 604 may be configured to receive a rod and prevent the rod from being released from the receiver 604. The receiver 604 may also enable the threaded member 606 to be threaded into the receiver 604 to prevent the rod from being released from the receiver 604 while enabling a rod to slide within the connector relative to the post 602.

Figure 23:
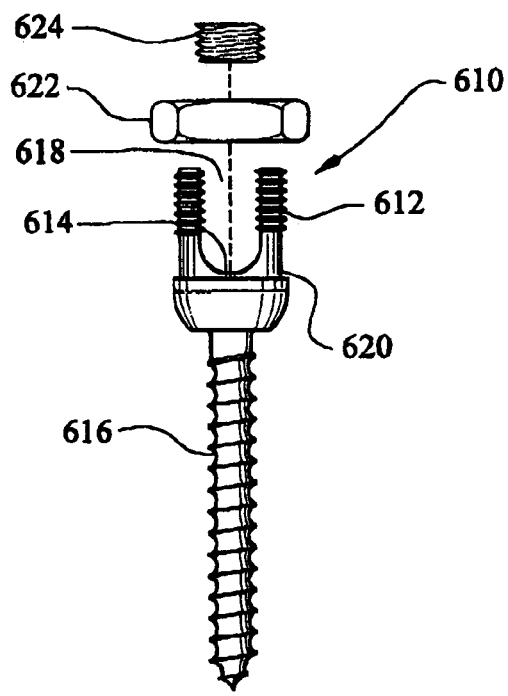
FIG. 23 is an exploded perspective view of another alternative connector.
Figure 24:
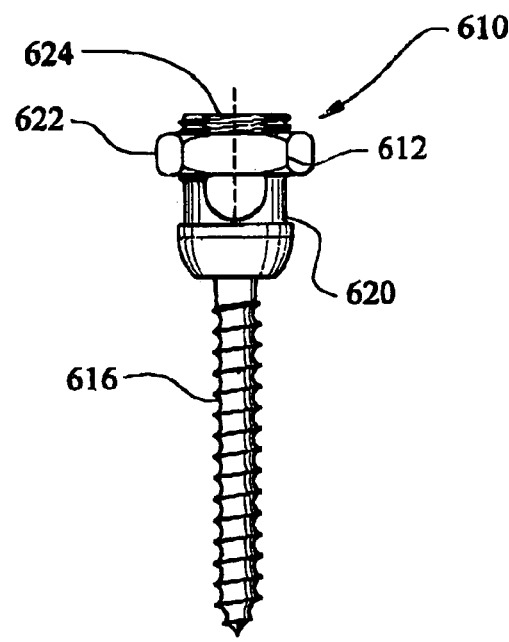
FIG. 24 is an assembled perspective view of the connector shown in FIG. 23.

FIGS. 23 and 24 show a connector 610 formed from a body 612 having a hollow cavity 614 configured to receive a post 616. The post 616 may have a generally spherical head configured to fit into and be retained by the body 612. The body 612 also includes slots 618, 620 formed in the body 612 and configured to accept a rod. The inner surface of the body 612 may include threads to which a set screw 624 may be attached. The outer surface of the body 612 may include threads to which a nut 622 may be attached. The nut 622 prevents the body 612 from deflecting and thereby enabling the set screw 624 to be released. In some embodiments, the nut 622 and set screw 624 are not tightened completely. Rather, the nut 622 and set screw 624 are left loose so that a rod inserted into the slots 618 and 620 is able to slide relative to the connector 600 to enable a facet joint of a patient to be strengthened without requiring fusion of two or more vertebrae.

Figure 25A:
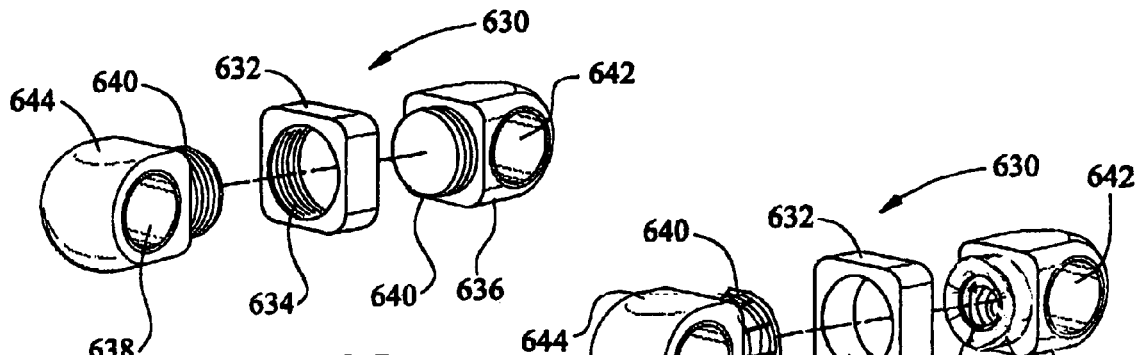
FIG. 25A is an exploded perspective view of yet another alternative connector.
Figure 25B:
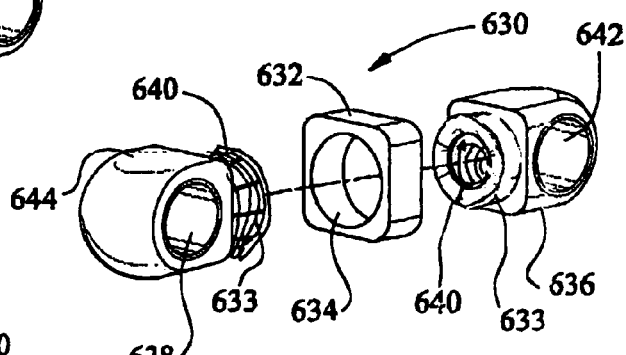
FIG. 25B is an exploded perspective view of still another alternative connector.
Figure 25C:
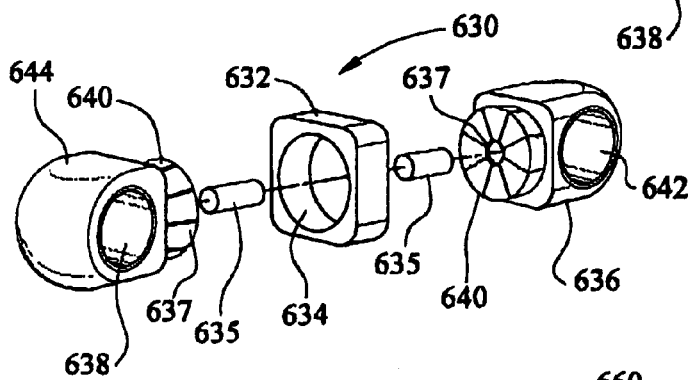
FIG. 25C is an exploded perspective view of another alternative connector.
Figure 26:
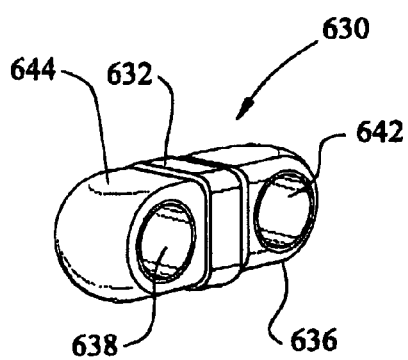
FIG. 26 is an assembled perspective view of the connector shown in FIG. 25.

FIGS. 25A, B, C, and 26 show a connector 630 formed from a body 632 having an aperture 634 extending through the body 632, a first rotatable end 636 coupled to a first end of the connector 630, and a second rotatable end 638 coupled to a second end of the connector 630. In at least one embodiment, the first rotatable end 636 may be coupled directly to the second rotatable end 638. The first and second rotatable ends 636 may include threaded posts 640 capable of being attached to the body 632. In alternative embodiments, the first and second rotatable ends 636 may be coupled to the body 632 with a pin 633 having barbs configured to engage grooves in post 640, as shown in FIG. 25B. In yet another embodiment, as shown in FIG. 25C, the first and second rotatable ends 636 may be coupled to the body with a pin 635 inserted into a shaft having a plurality of grooves 637 causing the grooves 637 to expand. The first and second rotatable ends 636, 638 include apertures 642, 644, respectively, for receiving a rod passing between adjacent vertebrae or a post, such as, but not limited to, a screw, a hook, or other appropriate device, attached to a vertebrae. When the connector 630 is attached to a post and a rod is inserted through an aperture of the connector 630, both the rod and the connector 630 are able to slide relative to the post. Thus, the rod is able to slide generally parallel to the spine of a patient and the connector 630 is able to slide generally parallel to a longitudinal axis of the post.

Figure 27:
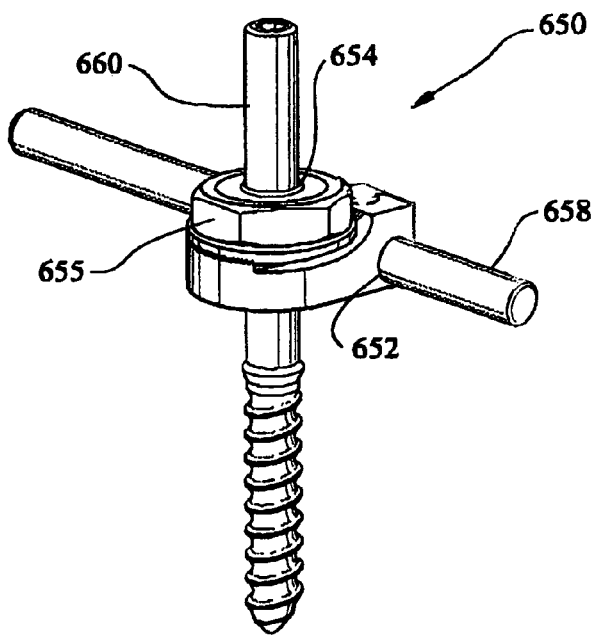
FIG. 27 is a perspective view of another alternative connector.

FIG. 27 shows a connector 650 having an aperture 652 for receiving a rod 658 and an aperture 654 for receiving a post 660, wherein the apertures 652, 654 are off-center from each other and generally orthogonal to each other. The aperture 654 may be formed from a plurality of prongs (not shown). The nut 655 may be tightened down onto the prongs, which in turn tighten against the post 660 and secure the connector 650 to the post 660. In some embodiments, the set screw 656 may be left loose or removed so that the rod may slide relative to the connector.

Figure 28:
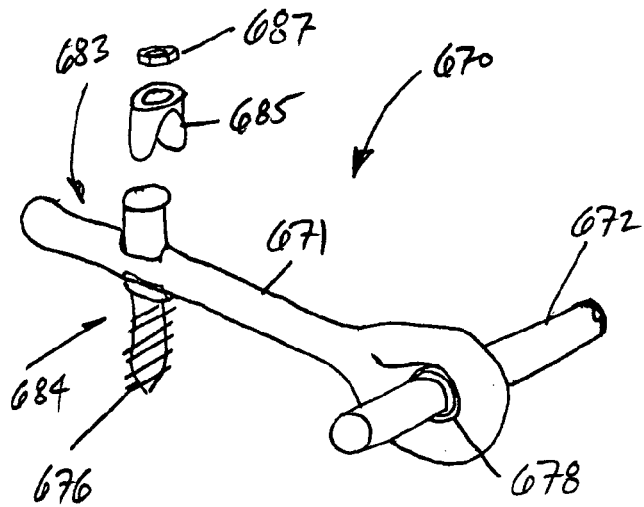
FIG. 28 is a perspective view of yet another alternative connector.
Figure 29:
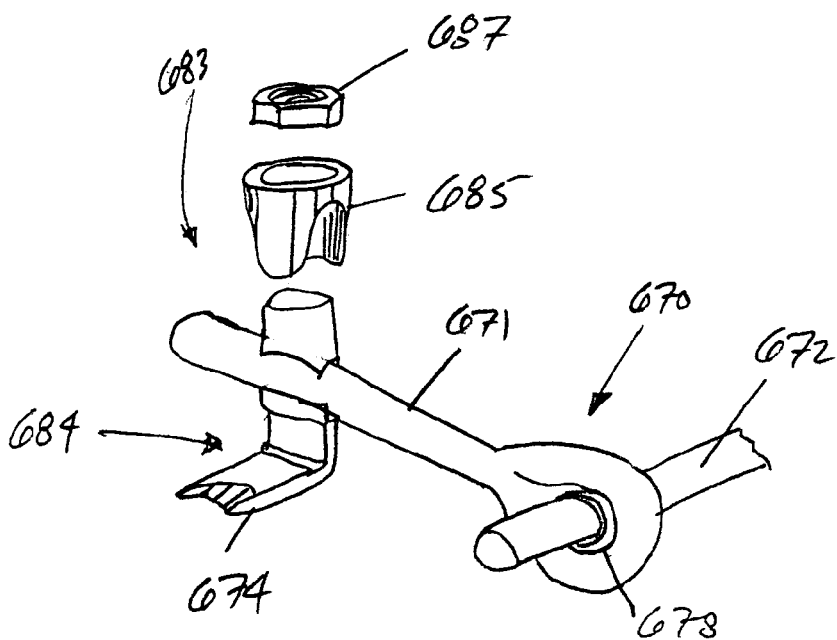
FIG. 29 is a perspective view of another alternative connector.

FIGS. 28 and 29 show a connector 670 for securing a rod 672 generally parallel to a spine. The connector 670 may be attached to a vertebrae with a hook 674, a screw 676, or other such device. The connector 670 may include an body 671 having aperture 678 for receiving a rod 672. In at least one embodiment, a longitudinal axis of the aperture 678 is generally orthogonal to the body 671. The body 671 may be formed as an elongated body and may be positioned generally orthogonal to an attachment device 684, which may be a post formed as a screw 676, a hook 674, an adhesive, or an expansion anchor. The attachment device 684 may be coupled to the body 671 using a mechanical assembly 683. For instance, the mechanical assembly 683 may be formed from an alignment washer 685 and a nut 687 usable to attach the attachment device 684 to the body 671. The attachment device 684 may be attached to the body 671 such that the attachment device is offset from a longitudinal axis of the aperture 678. In at least one embodiment, the set screw 684 may be attached to the connector 670 so that only the post 682 is prevented from movement, and the rod is able to slide relative to the connector 670 in a patient post-operatively.

Figure 30:
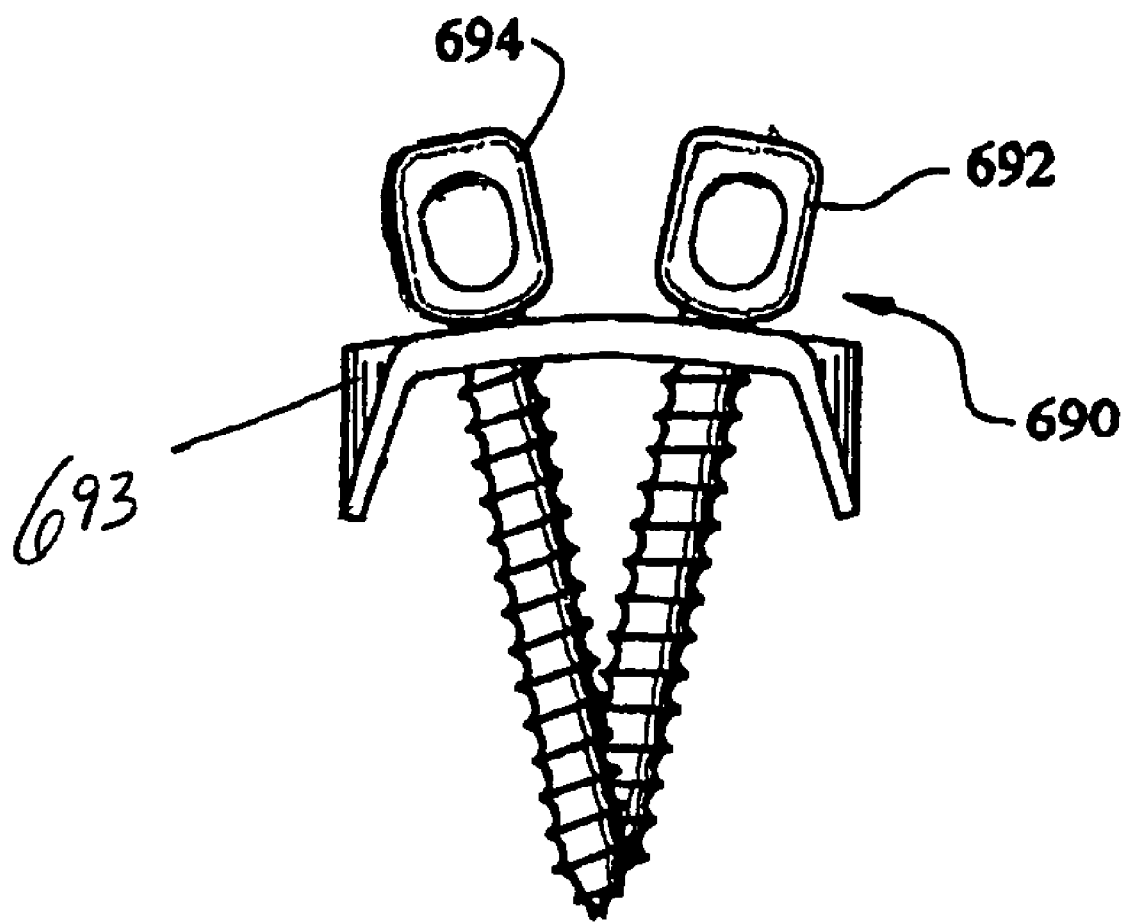
FIG. 30 is a perspective view of still another alternative connector.

FIG. 30 displays a connector 690 having two screws 692,694 capable of being attached to a vertebrae. Each screw 692, 694 may have an aperture 696, 697, respectively, for receiving a rod (not shown). For instance, the screw 692 may receive a first rod in the aperture 696, and the screw 694 may receive a second rod in the aperture 697. In at least one embodiment, a rod may be fixedly held in the aperture 696 while a second rod is permitted to slide freely through the aperture 697, or vice versa. In other embodiments, rods may be permitted to slide freely through both the aperture 696 and 697. The screws 692 and 694 may be held together with a central body 693.

Figure 31:
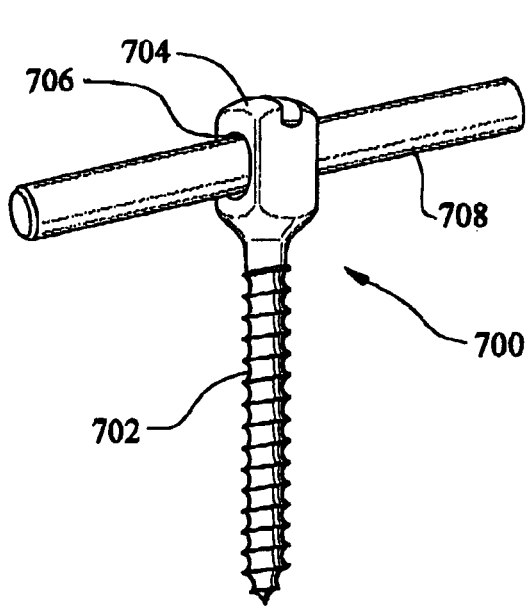
FIG. 31 is a perspective view of another alternative connector.
Figure 32:
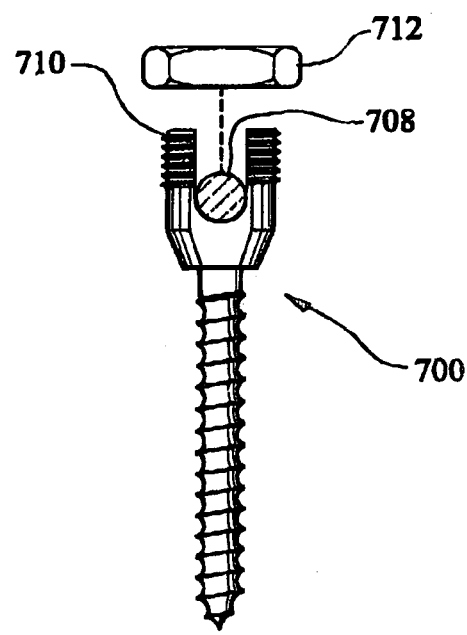
FIG. 32 is an exploded perspective view of yet another alternative connector.

FIGS. 31 and 32 display a connector 700 formed from a screw 702 having a head 704 with an aperture 706 sized to receive rod 708. The aperture 706 may be configured to slideably receive the rod 708. In at least one embodiment, as shown in FIG. 32, the connector 700 may include a slot 710 for receiving a rod 708. The rod 708 may be contained in the slot 710 using a releasable connector 712, which may be, but is not limited to, a nut. The nut 712 may include a nylon insert or other device enabling the nut 712 to be tightly attached to the head 704 without risk of the nut 712 backing off while also enabling a rod to slide in the aperture 706.

Figure 33:
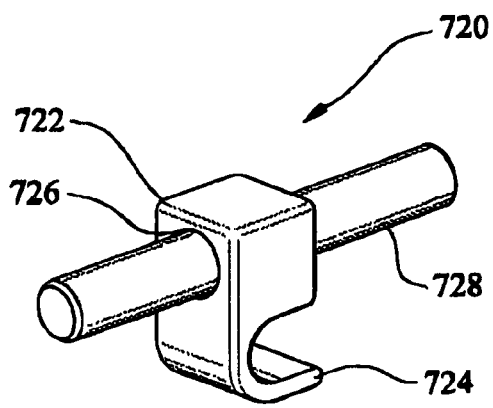
FIG. 33 is an exploded perspective view of another alternative connector.

FIG. 33 displays a connector 720 formed from a head 722 and a hook 724 for attaching the connector 720 to a vertebrae. The head 722 may include an aperture 726 through which a rod 728 may be passed. The rod 728 may remain in a sliding relationship to the body 722.

Figure 34:
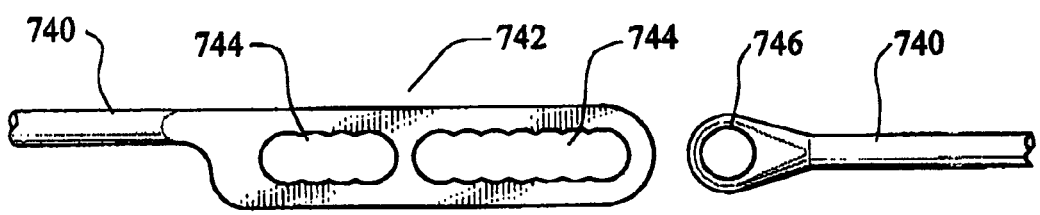
FIG. 34 is a top view of an alternative connector.

FIG. 34 shows a rod 740 having a connector receiving region 742 with one or more slots 744. The slots 744 are configured to receive a post or other member of a connector so that the rod 740 may be held generally parallel to a spine of a patient to strengthen a facet joint of the patient's spine. The rod 740 may also include a single aperture 746 for fixedly attaching the rod to a vertebrae or a sacrum when being used to attach the rod 740 to the spine.

Figure 42:
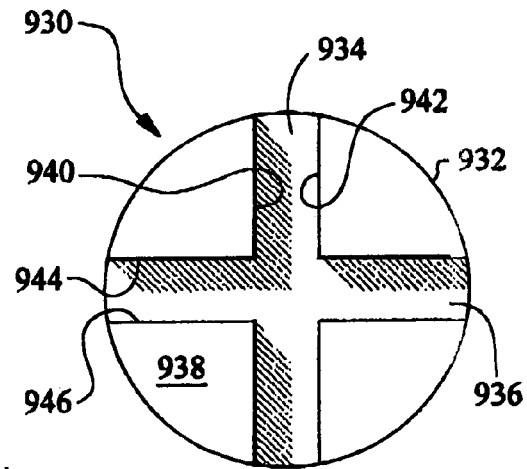
FIG. 42 is a front view of the connector shown in FIG. 41.

FIGS. 41–44 shows a connector 930 for slideably coupling a rod to a post for stabilizing a vertebral body. The connector 930 is formed from a body 932 having a first slot 934 and a second slot 936 in an exterior surface 938 of the body 932. In at least one embodiment, the first and second slots 934 and 936 are generally orthogonal to each other. However, in other embodiments, the first and second slots 934 and 936 are at other angles relative to each other. The first slot 934 may be formed from first and second opposing side walls 940, 942 defining a path of movement through which a rod may slide, and the second slot 936 may be formed from first and second opposing side walls 944, 946 defining a path of movement through which a post may slide. The first and second slots 934, 936, as shown in FIG. 42, may substantially prohibit any lateral movement, in the direction of the arrows, of a rod or post, respectively.

Figure 43:
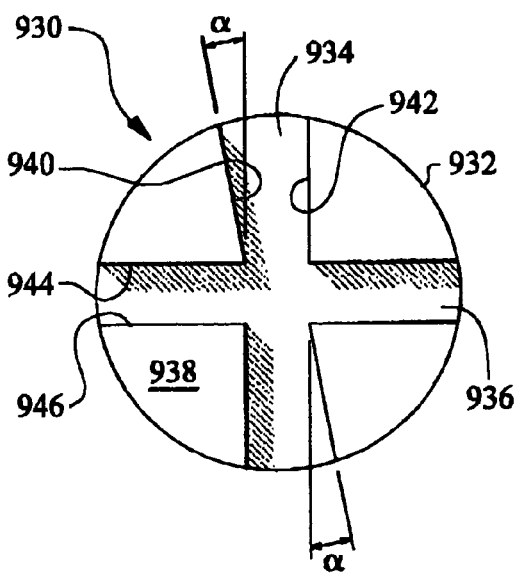
FIG. 43 is a front view of an alternative embodiment of the connector shown in FIGS. 41 and 42.
Figure 44:
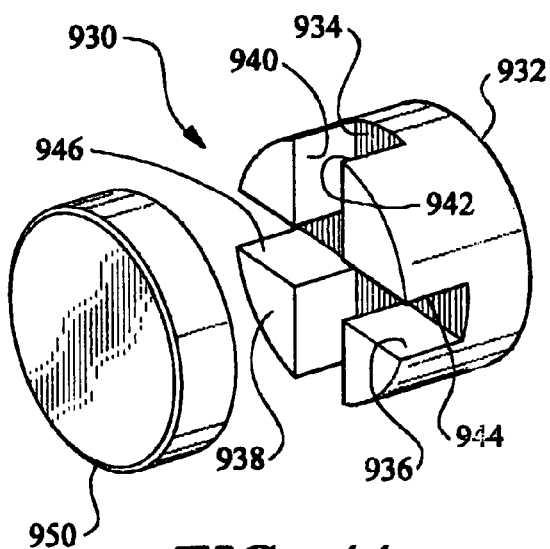
FIG. 44 is a perspective view of an alternative embodiment of the connector shown in FIG. 41.

In other embodiments, the first or second slot 934, 936, or both may be configured to allow a predetermined amount of lateral movement. For instance, as shown in FIG. 43, an upper part of the first side wall 940 and a lower part of the second wall 942 may be at an angle α relative to a longitudinal axis of the slot 934, thereby enabling a rod in the slot 934 to move through angle α. In at least one embodiment angle α may be any angle less than about 45 degrees, and may be between about one degree and about ten degrees. In some embodiments, the upper and lower sections of both the first and second side walls 940 and 942 may be at angles α relative to a longitudinal axis of the first slot 934. Side wall 944 or side wall 946, or both, of the second slot 936 may be at an angle α relative to a longitudinal axis of the second slot 936. In at least one embodiment, the body 932 may be elastic thereby enabling a limited amount of lateral movement of a rod or post in the first or second slot 934,936. In addition, the elastic material provides a method of dampening movement of a post or rod within the first or second slots 934, 936.

In yet another embodiment, a second body 950 may be used to secure a rod or post in the first and second slots 934, 936. The second body 950 may be attached to the first body 932 in any one of a number of ways. For instance, the second body 950 may be affixed to the first body 932 in a permanent manner using a permanent adhesive. In an alternative embodiment, the second body may be affixed to the first body 932 using a releasable connector, such as, but not limited to, a bolt, a screw, or other appropriate device. The second body may or may not have slots that align with the first and second slots 934, 936 in the first body 932.

The connectors shown in FIGS. 1–44 may be referred to as vertebral anchors. These vertebral anchors may be capable of being attached to a vertebrae, which may also be referred to as a vertebral body, through a number of different mechanical, chemical, and other methods. For instance, a vertebral anchor may be attached to a vertebral body using a post, a screw, a bolt, an adhesive, a cement, or other appropriate device. The vertebral anchor may also include a device for attaching the vertebral anchor to at least one slideable device to form a slideable relationship with the slideable device post-operatively in a patient. This device may be an aperture for accepting a rod, as shown in FIGS. 1–44, a slideable surface, a slot, a groove, or other appropriate device. The device for attaching the vertebral anchor to at least one slideable device to form a slideable relationship may also be independent of the mechanism used to attach the vertebral anchor to a vertebral anchor. The portion of the vertebral anchor to which at least one slideable device may be attached may be positioned such that the slideable device does not bear against the vertebral body. Rather, the slideable device bears against the vertebral anchor.

This invention can be embodied in other forms without departing from the spirit or essential attributes thereof and, accordingly, reference should be had to the following claims rather than the foregoing specification as indicating the scope of the invention.

I claim:

1. A method of stabilizing a vertebral body, comprising:
   securing a first rod to a first vertebrae in a manner that substantially prevents movement of the first rod relative to the first vertebrae;
   securing a second rod to a second vertebrae; and
   slideably coupling the first rod and the second rod together at a first connector positioned between a first point where the first rod is coupled to the first vertebrae and a second point where the second rod is coupled to the second vertebrae;
   wherein the first rod and the second rod remain in a slideable relationship relative to each other post-operatively.

2. The method of claim 1, wherein slideably coupling the first rod and the second rod together at a connector comprises inserting a portion of the first rod through a first aperture in the connector forming a slideable connection and inserting a portion of the second rod through a second aperture in the connector.

3. The method of claim 2, wherein inserting a portion of the second rod through the second aperture in the connector comprises forming a slideable connection between the second rod and the second aperture.

4. The method of claim 2, wherein inserting a portion of the second rod through the second aperture in the connector comprises fixedly attaching the second rod to the second aperture.

5. The method of claim 1, further comprising installing a spinal joint stabilization device displaced laterally from the first connector to enable post-operative movement of the first and second vertebrae relative to each other and to enable the first and second rods to move relative to each other.

6. The method of claim 5, wherein installing a spinal joint stabilization device comprises securing a first rod to a first vertebrae in a manner that substantially prevents movement of the first rod relative to the first vertebrae, securing a second rod to a second vertebrae, slideably coupling the first rod and the second rod together at a second connector positioned between a first point where the first rod is coupled to the first vertebrae and a second point where the second rod is coupled to the second vertebrae; and wherein the first rod and the second rod remain in a slideable relationship relative to each other in a patient post-operatively.

7. The method of claim 5, further comprising installing a transverse member coupling the spinal joint stabilization device with the first connector.

8. The method of claim 1, wherein securing a first rod to a first vertebrae comprises attaching a first post to the first vertebrae and attaching the first rod to the first post in a manner enabling the first rod to slide relative to the first post generally parallel to a longitudinal axis of the first rod post-operatively.

9. The method of claim 8, wherein attaching the first rod to the first post comprises passing the first rod through an aperture in the first post.

10. The method of claim 8, wherein securing a second rod to a second vertebrae comprises attaching a second post to the second vertebrae and attaching the second rod to the second post in a manner enabling the second rod to slide relative to the second post along a longitudinal axis of the second rod post-operatively.

11. The method of claim 10, wherein attaching the second rod to the second post comprises passing the second rod through an aperture in the second post.

12. The method of claim 1, further comprising limiting movement of the first and second vertebrae relative to each other by installing movement limiting devices on at least the first rod.

13. The method of claim 12, further comprising installing movement limiting devices on the first and second rods.

14. The method of claim 1, wherein securing a first rod to a first vertebrae comprises attaching the first rod to a post having a head movable in at least three axes post-operatively.

15. The method of claim 1, wherein securing a first rod to a first vertebrae comprises attaching the first rod to a post having a head enabling the first rod to move post-operatively generally along a longitudinal axis of the first rod.

16. The method of claim 15, wherein securing a second rod to a second vertebrae comprises securing the second rod to a past having a head enabling the second rod to move post-operatively generally along a longitudinal axis of the second rod.

* * * * *

UNITED STATES PATENT AND TRADEMARK OFFICE
CERTIFICATE OF CORRECTION

| | | |
|---|---|---|
| PATENT NO. | : 7,083,622 B2 | Page 1 of 1 |
| APPLICATION NO. | : 09/346256 | |
| DATED | : August 1, 2006 | |
| INVENTOR(S) | : Simonson | |

It is certified that error appears in the above-identified patent and that said Letters Patent is hereby corrected as shown below:

In the claims

Claim 1, column 19, line 23, after "a first connector" add --having at least two aperatures--.
Claim 2, column 19, line 32, replace "a first" with --the first--.
Claim 2, column 19, line 34, replace "a second" with --the second--.
Claim 16, column 20, line 47, replace "past" with --post--.

Signed and Sealed this

Twenty-eighth Day of November, 2006

JON W. DUDAS
*Director of the United States Patent and Trademark Office*